US010458962B2

(12) United States Patent
Sun

(10) Patent No.: US 10,458,962 B2
(45) Date of Patent: Oct. 29, 2019

(54) TEMPERATURE CONTROL FOR SURFACE ACOUSTIC WAVE SENSOR

(71) Applicant: Pulmostics Limited, Dublin (IE)

(72) Inventor: Yin Sun, Bridgewater, NJ (US)

(73) Assignee: Pulmostics Limited, Dublin (IE)

(*) Notice: Subject to any disclaimer, the term of this patent is extended or adjusted under 35 U.S.C. 154(b) by 276 days.

(21) Appl. No.: 15/653,256

(22) Filed: Jul. 18, 2017

(65) Prior Publication Data

US 2018/0024100 A1 Jan. 25, 2018

Related U.S. Application Data

(60) Provisional application No. 62/365,602, filed on Jul. 22, 2016.

(51) Int. Cl.
*G01N 30/76* (2006.01)
*G01N 29/02* (2006.01)
(Continued)

(52) U.S. Cl.
CPC .......... *G01N 30/76* (2013.01); *G01N 29/022* (2013.01); *G01N 29/036* (2013.01);
(Continued)

(58) Field of Classification Search
CPC ........ G01N 1/10; G01N 1/2202; G01N 21/65; G01N 2291/02809; G01N 29/022; G01N 29/036; G01N 30/74; G01N 30/76; G01N 30/78; G01N 30/8675; G01N 2030/025; G01N 2030/8854
See application file for complete search history.

(56) References Cited

U.S. PATENT DOCUMENTS 5,289,715 A     3/1994 Staples et al.
5,455,673 A *  10/1995 Alsmeyer ................ G01J 3/44
                                            356/301

(Continued)

FOREIGN PATENT DOCUMENTS

EP     1636569     6/2008
EP     2083266     7/2009

*Primary Examiner* — Francis C Gray
(74) *Attorney, Agent, or Firm* — Stetina Brunda Garred & Brucker

(57) ABSTRACT

A method for identification of chemicals in a sample using a gas chromatograph and a surface acoustic wave (SAW) sensor coupled with the gas chromatograph to define a gas chromatography (GC)/SAW system. The method includes receiving a temperature profile defining a varying target temperature as a function of time, separating one or more eluted components from a sample with the gas chromatograph, adjusting a temperature of the SAW sensor in accordance with the temperature profile as the one or more eluted components are separated from the sample by the gas chromatograph, generating SAW frequency response data with the SAW sensor, the SAW frequency response data including one or more peaks corresponding respectively to the one or more eluted components separated from the sample, and identifying a set of one or more candidate chemicals for an eluted component of interest based on a corresponding peak of the SAW frequency response data.

20 Claims, 13 Drawing Sheets

(51) Int. Cl.
*G01N 29/036* (2006.01)
*G01N 29/24* (2006.01)
*G01N 29/32* (2006.01)
G01N 30/02 (2006.01)
G01N 30/86 (2006.01)
G01N 30/88 (2006.01)

(52) U.S. Cl.
CPC ....... G01N 29/2462 (2013.01); G01N 29/326 (2013.01); *G01N 30/8675* (2013.01); *G01N 2030/025* (2013.01); *G01N 2030/8854* (2013.01); *G01N 2291/0215* (2013.01)

(56) References Cited

U.S. PATENT DOCUMENTS

| | | | |
|---|---|---|---|
| 5,827,946 A | 10/1998 | Klee et al. | |
| 6,161,437 A | 12/2000 | Brennan et al. | |
| 6,955,787 B1 * | 10/2005 | Hanson | G01N 29/022 29/592 |
| 7,037,797 B1 | 5/2006 | Shooshtarian et al. | |
| 7,299,711 B1 | 11/2007 | Linker et al. | |
| 7,343,779 B1 * | 3/2008 | Yu | G01N 30/08 422/89 |
| 7,377,169 B2 * | 5/2008 | Myers | G01N 29/024 73/587 |
| 7,692,517 B2 * | 4/2010 | Martin | H03B 5/326 333/133 |
| 7,814,901 B2 * | 10/2010 | Lieberman | A61M 11/005 128/200.16 |
| 2001/0030285 A1 * | 10/2001 | Miller | G01N 27/624 250/288 |
| 2008/0289397 A1 * | 11/2008 | Hassan | G01G 3/16 73/23.4 |
| 2009/0189064 A1 * | 7/2009 | Miller | G01N 27/624 250/282 |
| 2010/0111133 A1 | 5/2010 | Yuhas et al. | |
| 2013/0157254 A1 * | 6/2013 | Sengupta | G01N 21/658 435/5 |
| 2018/0095060 A1 * | 4/2018 | Fan | G01N 30/463 |

* cited by examiner

TEMPERATURE CONTROL FOR SURFACE ACOUSTIC WAVE SENSOR

CROSS-REFERENCE TO RELATED APPLICATION(S)

This application relates to and claims the benefit of U.S. Provisional Application No. 62/365,602 filed Jul. 22, 2016 and entitled "SENSOR TEMPERATURE RAMP DURING ANALYSIS FOR IMPROVED PERFORMANCE," the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to surface acoustic wave (SAW) sensors employed in the identification of chemicals, and more particularly, to temperature control for a SAW sensor.

2. Related Art

Surface acoustic wave (SAW) sensors are widely used in chemical detection sensor applications. A SAW sensor is generally defined by an input transducer, which converts a known input electronic signal into an acoustic/mechanical wave, and an output transducer that converts that wave back into an electronic signal for further processing. The transducers, which are interdigitated, are disposed on a piezoelectric substrate such as quartz. A SAW sensor may be implemented in a resonator configuration, where a first set of reflector electrodes and a second set of reflector electrodes surround a set of interdigitated electrodes, or in a delay line configuration, where the input interdigitated transducer electrodes are spaced apart from the output interdigitated transducer electrodes.

The frequency of the output electronic signal of the SAW sensor varies due to mass loading on the surface of the SAW sensor. When the surface is clean and free from additional mass loading, the output electronic signal has known characteristics, that is, a known frequency. With additional mass loading, the oscillation frequency is reduced, and there is understood to be a linear relation between the additional mass and the reduction in oscillation frequency. This behavior may be utilized for detecting and identifying various chemical compounds.

There are two major types of detectors that use SAW sensors. One is a sensor array using multiple SAW sensors with different surface coatings. Chemicals are selectively adsorbed by the coating materials, resulting in changes in the SAW oscillation frequency. Different coatings may adsorb different amounts of chemicals and, thus, the frequency of each SAW sensor in the array may change differently. The detection of a sample is based on the pattern of the signals of all the sensors in the sensor array.

The other major type of detector that uses SAW sensors is a gas chromatography/surface acoustic wave (GC/SAW) system. A GC/SAW system combines a SAW sensor with gas chromatography (GC). A vaporized sample passes through a GC column of a gas chromatograph in which different components of the sample are retained for different lengths of time depending on their chemical-physical properties. As each component elutes from the GC column, it contacts the SAW sensor. When the SAW sensor temperature is below the dew point of the eluted vapor, the chemical component will condense on the surface of the SAW sensor, resulting in a change in the oscillation frequency of the SAW sensor. Detection and identification are made based on the change in oscillation frequency and the retention time of the chemical in the GC column, with the mass loading of the chemical component by condensation being the basis for the sensor response.

There are generally three contributors to the mass loading on the surface of the SAW sensor in a GC/SAW system. First, there is condensation due to the saturation of chemical components in the eluted vapor in contact with the SAW sensor. Chemical components loaded on the surface of the SAW sensor via condensation evaporate when the concentration in the vapor is below the saturation level. It is not necessary for the SAW sensor to be heated to release the condensed chemical components, and the release is understood to be complete without any residue remaining on the surface of the SAW sensor. If the chemical components load on the surface of the SAW sensor by this mechanism alone, short and long term operational stability is possible.

Second, there is physical adsorption due to weak Van der Waals forces between the surface of the SAW sensor and the molecules in the eluted vapor. Such adsorption may require external energy to reverse and completely release the adsorbed chemical components. As the bond is based upon weak Van der Waals forces, only a slight increase in temperature of the SAW sensor may be needed to break the bond. It is understood that residue does not remain on the surface, and therefore raising the temperature of the SAW sensor by a prescribed degree after each analysis cycle is considered sufficient to clean the chemical components physically adsorbed on the surface of the SAW sensor.

Third, there is chemical adsorption due to the formation of chemical bonds between the active sites of the SAW surface (including the substrate surface and the interdigitate electrodes) and the molecules in the eluted vapor. For example, although a quartz substrate, which is one of the most used piezoelectric materials for a SAW sensor, is generally regarded as inert, it is slightly acidic and highly adsorptive due to the presence of hydroxyl groups (—OH). Such reactive groups are understood to interact with chemicals having different functional groups such as amine (—NH), carboxylic acid (—COOH), hydroxyl (—OH), or thiol (—SH) via hydrogen bonding. The reaction between the surface of the SAW sensor and such functional groups results in chemical adsorption of compounds that contain such functional groups onto the surface of the SAW sensor. Chemical components containing such functional groups in a sample being analyzed may bond to the surface of the SAW sensor and cannot be removed without significant external energy. Furthermore, the chemical compounds that remain on the surface of the SAW sensor may create different active sites thereon and react with other chemical compounds, thereby increasing the chemical adsorption capability of the SAW sensor.

As chemical components elute from a GC column in sequence, they can be captured by the surface of the SAW sensor via one or more of the three mechanism described above. All three mechanisms potentially create interference/error in the SAW frequency response under static SAW temperature. For chemical components captured on the surface of the SAW sensor by condensation, the evaporation is controlled by the evaporation kinetic, which may be slower than that of condensation. Therefore, the peak in the SAW frequency response corresponding to an eluted chemical component condensing on the SAW sensor may be asymmetric, with the peak tail longer than the peak front. As for chemical components captured through physical or chemical adsorption, the captured chemical component may not leave the surface under the same SAW sensor temperature condition at which it was captured. Therefore, such captured chemical components may stay on the surface of the SAW sensor and may form plateaus in the SAW frequency response. When the SAW sensor is operated at static temperature, saturation of the SAW sensor may occur if the mass loading becomes so high that the oscillation frequency reduces to a very low level that cannot be reported accurately. Such a saturation peak may take a long time to disappear and may make detection of subsequently eluted chemical components difficult or impossible.

Conventionally, a SAW sensor may be cleared down at the end of each analysis by increasing its temperature to a much higher level (e.g. from 70° C. sensor temperature during analysis to 150° C. clear-down temperature for 30 seconds). In general, this clear-down procedure recovers the SAW sensor to its initial state without obvious short term sensor drift. However, it is possible for strong bonds to form between high affinity chemicals and the surface of the SAW sensor such that the surface cannot be cleared to its initial status. Thus, over time and multiple analysis cycles, there may be an accumulation of residual compounds that, in turn, affect the oscillation frequency, resulting in long term instrument drift. Heavily contaminated sensors require heating for longer durations and at higher temperatures. Where heating the SAW sensor is insufficient, the SAW sensor may be washed with solvents such as acetone. To the extent a solvent wash is also insufficient, the SAW sensor may require replacement.

In addition to the conventional need for time-consuming clear-down procedures and the risk of instrument failure, the accumulation of chemical residue on the SAW sensor causes problems within a single analysis by the GC/SAW system. For example, as mentioned above, saturation peaks in the SAW frequency response may effectively hide subsequent peaks, making them undetectable. Also, since quantitative peak analysis (e.g. mass estimation of the corresponding eluted chemical component) may be based on peak height or area, the increase in peak size due to accumulated residue of previously eluted chemical components may result in a large quantitative error.

BRIEF SUMMARY

The present disclosure contemplates various systems, methods, and apparatuses for overcoming the above drawbacks accompanying the related art. One aspect of the embodiments of the present disclosure is a method for identification of chemicals in a sample. The method includes receiving a temperature profile defining a varying target temperature as a function of time, separating one or more eluted components from a sample with a gas chromatograph, and adjusting a temperature of a surface acoustic wave sensor in accordance with the temperature profile as the one or more eluted components are separated from the sample by the gas chromatograph. The surface acoustic wave sensor is coupled with the gas chromatograph to define a gas chromatography/surface acoustic wave system in which the one or more eluted components separated from the sample by the gas chromatograph accumulate at a condensation spot on the surface acoustic wave sensor. The method further includes generating surface acoustic wave frequency response data with the surface acoustic wave sensor. The surface acoustic wave frequency response data includes one or more peaks corresponding respectively to the one or more eluted components separated from the sample by the gas chromatograph. The method further includes identifying a set of one or more candidate chemicals for an eluted component of interest based on a corresponding peak of the surface acoustic wave frequency response data.

Another aspect of the embodiments of the present disclosure is a system for identification of chemicals in a sample. The system includes a gas chromatograph and a surface acoustic wave sensor coupled with the gas chromatograph to define a gas chromatography/surface acoustic wave system in which one or more eluted components separated from a sample by the gas chromatograph accumulate at a condensation spot on the surface acoustic wave sensor. The surface acoustic wave sensor generates surface acoustic wave frequency response data including one or more peaks corresponding respectively to the one or more eluted components separated from the sample by the gas chromatograph. The system further includes a thermoelectric cooler operable to adjust a temperature of the surface acoustic wave sensor, a temperature controller that receives a temperature profile defining a varying target temperature as a function of time and instructs the thermoelectric cooler to adjust the temperature of the surface acoustic wave sensor in accordance with the temperature profile as the one or more eluted components are separated from the sample by the gas chromatograph, and a candidate chemical identifier, communicatively coupled to the surface acoustic wave sensor, a set of one or more candidate chemicals for the eluted component of interest being identified by the candidate chemical identifier based on a corresponding peak of the surface acoustic wave frequency response data.

Another aspect of the embodiments of the present disclosure is a non-transitory program storage medium on which are stored instructions executable by a processor or programmable circuit to perform operations for identification of chemicals in a sample. The operations include receiving a temperature profile defining a varying target temperature as a function of time and issuing a temperature control command to adjust a temperature of a surface acoustic wave sensor in accordance with the temperature profile as one or more eluted components are separated from a sample by a gas chromatograph. The surface acoustic wave sensor is coupled with the gas chromatograph to define a gas chromatography/surface acoustic wave system in which the one or more eluted components separated from the sample by the gas chromatograph accumulate at a condensation spot on the surface acoustic wave sensor. The operations further include receiving surface acoustic wave frequency response data generated by the surface acoustic wave sensor. The surface acoustic wave frequency response data includes one or more peaks corresponding respectively to the one or more eluted components separated from the sample by the gas chromatograph. The operations further include identifying a set of one or more candidate chemicals for an eluted component of interest based on a corresponding peak of the surface acoustic wave frequency response data.

Another aspect of the embodiments of the present disclosure is an apparatus including the non-transitory program storage medium and a processor or programmable circuit for executing the instructions. The apparatus may further include a thermoelectric cooler configured to receive the temperature control command and adjust the temperature of the surface acoustic wave sensor based on the temperature control command. The apparatus may further include the surface acoustic wave sensor. The apparatus may further include the gas chromatograph.

The present disclosure will be best understood accompanying by reference to the following detailed description when read in conjunction with the drawings.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The present disclosure encompasses various embodiments of systems, methods, and apparatuses for identification of chemicals in a sample. The detailed description set forth below in connection with the appended drawings is intended as a description of the several presently contemplated embodiments of these methods, and is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
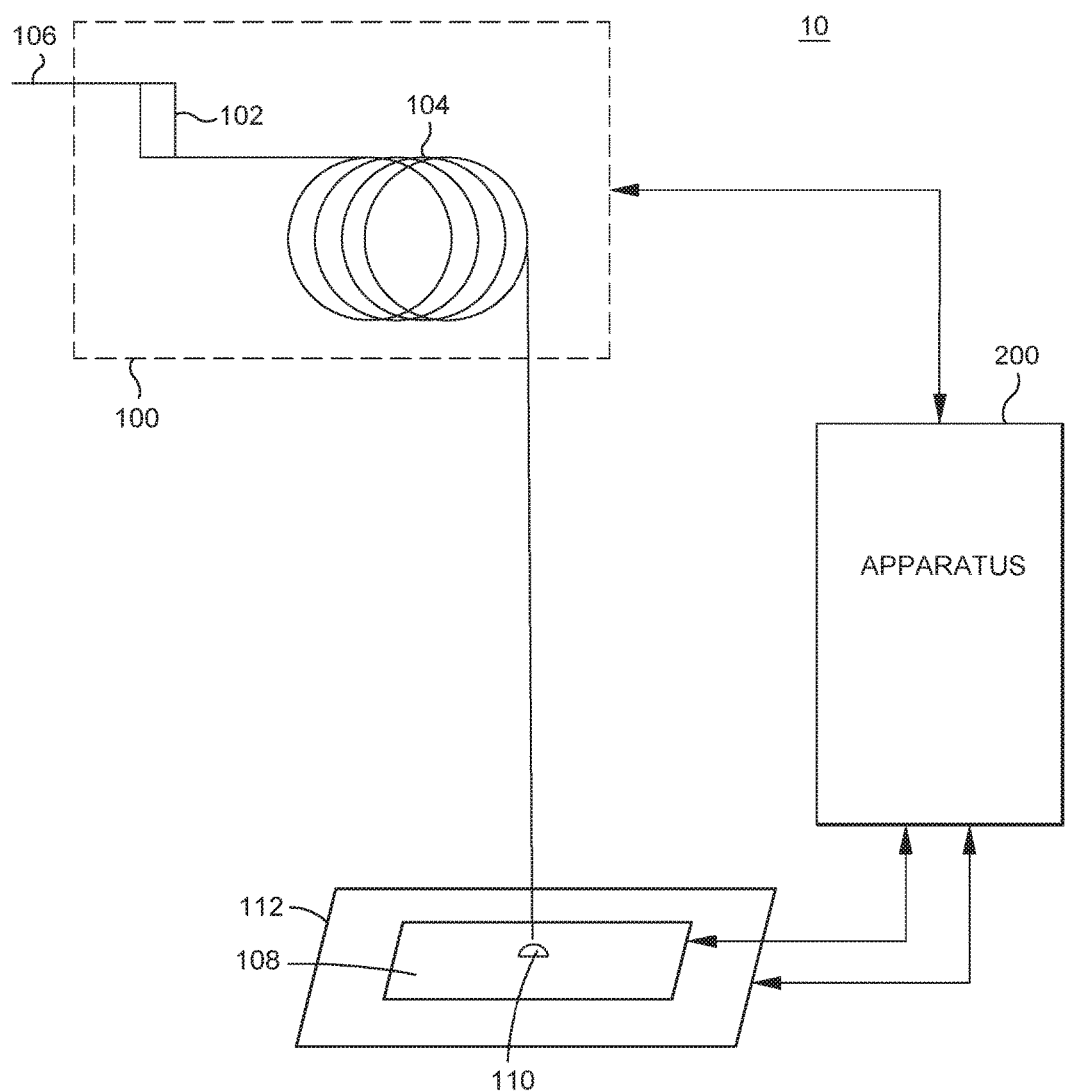
FIG. 1 illustrates a system for identification of chemicals in a sample according to an embodiment of the present disclosure.

FIG. 1 illustrates a system 10 for identification of chemicals in a sample according to an embodiment of the present disclosure. The system 10 includes a gas chromatograph 100, which may include an injection port 102 and a gas chromatography (GC) column 104. Upon being injected into the gas chromatograph 100 via the injection port 102, the sample is vaporized and carried by a carrier gas 106 through the GC column 104, where different components of the sample are retained for different lengths of time depending on their chemical-physical properties. The system 10 illustrated in FIG. 1 further includes a surface acoustic wave (SAW) sensor 108 coupled with the gas chromatograph 100 to define a GC/SAW system in which one or more eluted components separated from the sample by the gas chromatograph 100 accumulate at a condensation spot 110 on the SAW sensor 108. The SAW sensor 108 may, for example, be arranged in proximity to the output of the GC column 104 such that the condensation spot 110 is approximately the size of an internal dimension of the GC column 104. Chemical components of the sample eluting from the GC column 104 arrive at the condensation spot 110, where they condense as long as the temperature of the SAW sensor 108 is lower than the dew point of the chemical component. To this end, the system may include a thermoelectric cooler 112 by which the temperature of the SAW sensor 108 can be adjusted. Electronics (not shown) associated with the SAW sensor 108 may generate SAW frequency response data including one or more peaks corresponding respectively to one or more chemical components that condense at the condensation spot 110 as they elute from the GC column 104. A peak formed by the decrease of the oscillation frequency of the SAW sensor 108 may be defined by the start of the detectable frequency decrease due to condensation/adsorption and the end of the frequency increase due to the evaporation of the condensed/adsorbed chemical. For convenience, the decrease of frequency is normally presented as an increase in the y-direction in an x-y coordinate system to form a peak instead of a valley.

The gas chromatograph 100 and SAW sensor 108 may be of any type known in the art. Selection of the injection port 102, GC column 104, and carrier gas 106 may be in accordance with known principles of gas chromatography and GC/SAW systems and may depend on the nature of the sample and the particular application. For example, the diameter of the GC column 104 and other aspects of the GC/SAW system may be selected to support fast GC.

The system 10 of FIG. 1 includes an apparatus 200 which may support the qualitative and/or quantitative identification of chemicals in the sample and/or temperature control functionality associated with the thermoelectric cooler 112. The apparatus 200 may be operatively connected to each of the other components of the system 10, including the SAW sensor 108, the gas chromatograph 100, and/or the thermoelectric cooler 112. Thus, the apparatus 200 may be used for post-processing of SAW frequency response data and/or control of the various system components, which may be in accordance with results of processing by the apparatus 200 and/or user input to the apparatus 200. The apparatus 200 may serve as a user terminal. The operative connection of the apparatus 200 may be a physical (e.g. wired) connection or a wireless connection over a network. The operative connection of the apparatus 200 may be a purely conceptual connection. For example, data generated by the SAW sensor 108, etc. may then be accessed, processed, etc. by the apparatus 200 (e.g. after being transferred by some data storage medium) in the case of post-processing, or vice versa in the case of system control by the apparatus 200.

Figure 2:
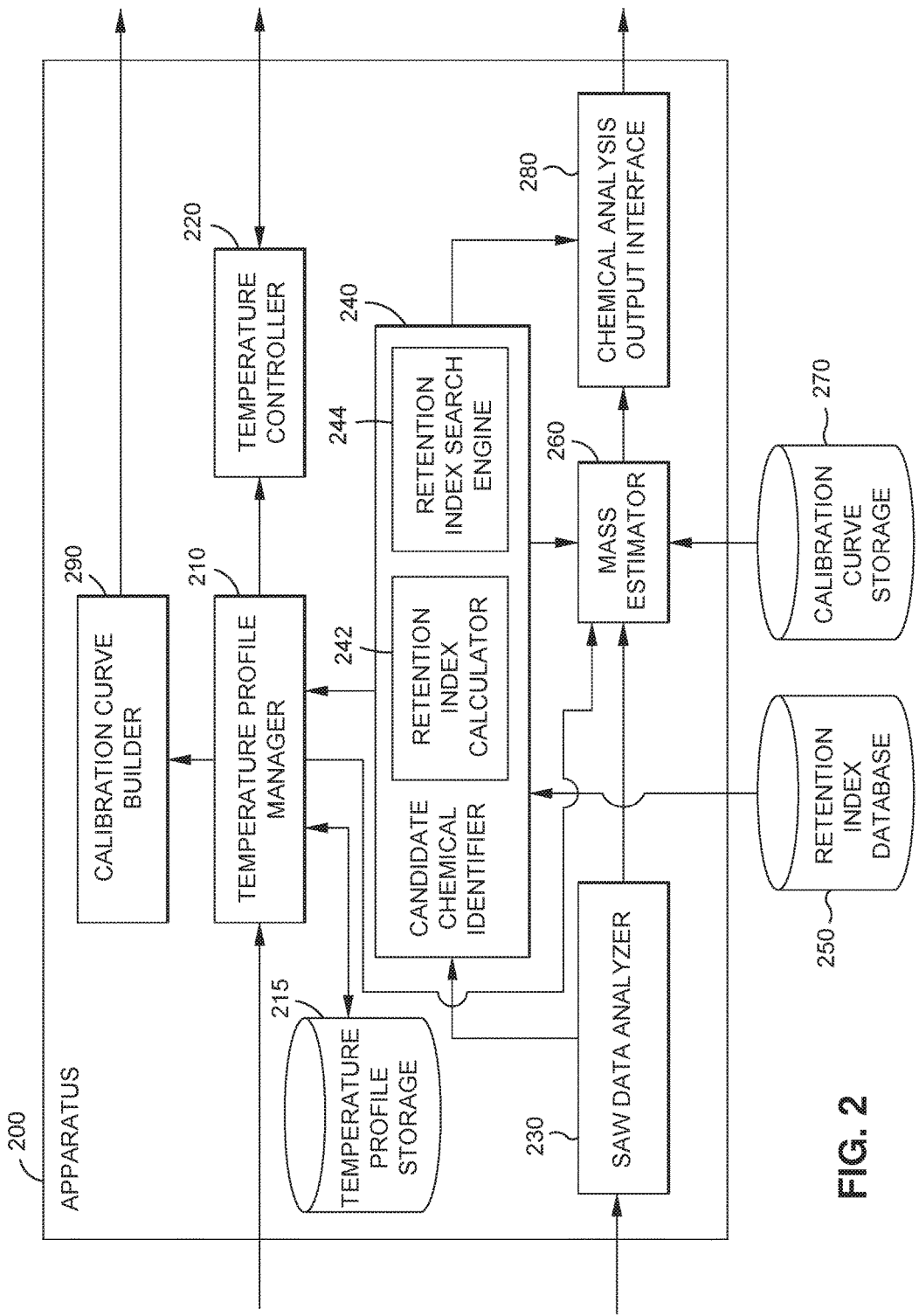
FIG. 2 illustrates an example apparatus for identification of chemicals in a sample according to an embodiment of the present disclosure.

FIG. 2 illustrates an example apparatus 200 for identification of chemicals in a sample according to an embodiment of the present disclosure. The apparatus 200 receives a temperature profile defining a varying target temperature as a function of time and adjusts a temperature of the SAW sensor 108 in accordance with the temperature profile, e.g. via the thermoelectric cooler 112, as one or more eluted components are separated from the sample by the gas chromatograph 100. The apparatus 200 may further receive SAW frequency response data and identify a set of candidate chemicals and/or estimate a mass for an eluted component of interest using the SAW frequency response data. On the basis of such qualitative and/or quantitative analysis, the apparatus 200 may modify the temperature profile and/or adjust settings of the other system components of FIG. 1. The apparatus 200 includes a temperature profile manager 210, a temperature profile storage 215, a temperature controller 220, a SAW data analyzer 230, a candidate chemical identifier 240, a mass estimator 260, a chemical analysis output interface 280, and a calibration curve builder 290 and may further include or have access to a retention index database 250 and a calibration curve storage 270.

The temperature profile manager 210 manages a temperature profile defining a varying target temperature as a function of time. The temperature profile manager 210 may, for example, function as a temperature profile input interface for receiving the temperature profile from outside the apparatus 200 and storing the received temperature profile in the temperature profile storage 215 for use by the apparatus 200. The temperature profile manager 210 may, for example, receive the temperature profile from an external storage or from a computer or server through a wired or wireless network such as the Internet, WAN, and/or LAN. As another example, the temperature profile manager 210 may receive the temperature profile as a series of user input commands for creating a temperature profile from scratch, e.g. via any combination of input device(s) including, for example, mouse, keyboard, touchscreen, eye tracking, voice, and/or gestures. The temperature profile manager 210 may further function as a temperature profile editor for modifying an existing temperature profile stored in the temperature profile storage 215.

The temperature controller 220 receives the temperature profile stored in the temperature profile storage 215 from the temperature profile manager 210. The temperature controller 200 then instructs the thermoelectric cooler 112 (see FIG. 1) to adjust the temperature of the SAW sensor 108 in accordance with the temperature profile as the one or more eluted components are separated from the sample by the gas chromatograph 100. The temperature controller 220 may, for example, issue a temperature control command to the thermoelectric cooler 112 to adjust the temperature of the SAW sensor 108 in accordance with the temperature profile. For example, the temperature profile may define a set point of the temperature controller 220, and the temperature controller 220 may issue temperature control commands to the thermoelectric cooler 112 as a function of the set point defined by the temperature profile and a feedback signal received from the thermoelectric cooler 112 (e.g. as a function of the difference between the set point and the feedback signal). The feedback signal may be generated, for example, based on a temperature sensor (not shown) of the thermoelectric cooler 112 or SAW sensor 108. In this way, the temperature controller 220 may control the thermoelectric cooler 112 to maintain a time-dependent temperature of the SAW sensor 108 corresponding to the temperature profile stored in the temperature profile storage 215.

The SAW data analyzer 230 receives SAW frequency response data generated by the SAW sensor 108 of the GC/SAW system. The SAW frequency response data includes one or more peaks corresponding respectively to one or more eluted components separated from a sample by the gas chromatograph 100 of the GC/SAW system. The SAW frequency response data is a representation of the frequency response of the SAW sensor 108 as a function of time and may be in the form of, for example, frequency in Hz versus GC retention time in seconds. Thus, in a case where the sampling frequency of the SAW sensor 108 is 50 Hz, the SAW frequency response data may include a series of frequency response samples at 20 millisecond intervals. The frequency response of the SAW sensor 108 may be, for example, a change in an oscillation frequency due to the accumulation of an eluted chemical component on the SAW sensor 108. The SAW data analyzer 230 may receive the SAW frequency response data from outside the apparatus 200. For example, the SAW data analyzer 230 may receive the SAW frequency response data directly from the other system components of FIG. 1, e.g. by wired or wireless connection with the SAW sensor 108 or associated electronics (not shown) thereof. Alternatively, the SAW frequency response data can be received from an external storage or received from a computer or server through a network such as the Internet, WAN, and/or LAN.

The SAW data analyzer 230 identifies the one or more peaks of the SAW frequency response data. For example, the SAW data analyzer 230 may identify peaks and valleys by approximating the SAW frequency response data with a polynomial, taking the derivative of the polynomial, and finding the points where the derivative of the polynomial is equal to zero (corresponding to maxima and minima of the polynomial). The SAW data analyzer 230 may thus characterize each of the one or more peaks by its GC retention time or sample number. The SAW data analyzer 230 may further characterize each of the one or more peaks by a peak height and/or a peak area (e.g. by integrating the polynomial approximating the SAW frequency response data from valley to valley around the peak).

The candidate chemical identifier 240 identifies a set of one or more candidate chemicals for an eluted component of interest based on the corresponding peak of the SAW frequency response data. The candidate chemical identifier 240 may, for example, identify sets of candidate chemicals for all of the eluted components, i.e. a set of candidate chemicals for each of the peaks found by the SAW data analyzer 230. Or, in a case where some peaks are uninteresting, the candidate chemical identifier 240 may identify sets of candidate chemicals for only a subset of the peaks found by the SAW data analyzer 230. The candidate chemical identifier 240 includes a retention index calculator 242 and a retention index search engine 244.

The retention index calculator 242 calculates a retention index for the eluted component of interest from the corresponding peak of the SAW frequency response data. A GC retention time of a peak found by the SAW data analyzer 230 may be converted into a retention index, e.g. Kovats retention index, that is independent of the specific gas chromatograph 100 and its operating conditions. The retention index calculator 242 may calculate the retention index by known methods. For example, n-alkanes may be injected into the gas chromatograph 100 together with the sample, and the peaks of the eluted n-alkanes may be found by the SAW data analyzer 230 together with the peaks corresponding to the chemical components of the sample. The retention index calculator 242 may calculate the retention index of a given peak of the sample based on its relationship to the peaks of the eluted n-alkanes.

The retention index database 250 may include, for example, a table of chemicals and corresponding known retention indices. The retention index search engine 244 searches the retention index database 250 for one or more matches between the determined retention index and chemicals in the retention index database 250. In this way, the candidate chemical identifier 240 may identify a set of one or more candidate chemicals for each of the eluted components.

In the example of the candidate chemical identifier 240 shown in FIG. 2, identification of candidate chemicals may be achieved with the use of retention indices. To this end, the candidate chemical identifier 240 includes the retention index calculator 242 and the retention index search engine 244 which has access to the retention index database 250. However, other methods of identifying candidate chemicals are known in the art, such as direct comparison of retention times with retention times of known chemicals eluted from the same gas chromatograph 100 under similar conditions. Therefore, in some embodiments, the candidate chemical identifier 240 may omit the retention index calculator 242 and the retention index search engine 244, and may thus have no need to access the retention index database 250.

The mass estimator 260 estimates a mass of an eluted component of interest based on the corresponding peak of the SAW frequency response data. As explained above, the SAW data analyzer 230 may characterize each of the one or more peaks of the SAW frequency response data by a peak height and/or a peak area. Meanwhile, the calibration curve storage 270 may store calibration curves for various chemicals. Each calibration curve maps peak height or peak area to mass or other quantitative measure (e.g. concentration) in a known relationship for that chemical at a specific temperature or temperature range. A calibration curve for a given temperature may be expressed as an equation $y=f(x)$, where y is peak height or area and x is mass or concentration, for example, or as an equivalent lookup table. Upon the successful identification of a candidate chemical for the eluted component of interest by the candidate chemical identifier 240, the mass estimator 260 may compare the peak (e.g. height or area) corresponding to the eluted component of interest to a calibration curve stored in the calibration curve storage 270 with reference to the corresponding temperature as indicated by the temperature profile stored in the temperature profile storage 215. For example, the mass estimator 260 may insert the height or area of the peak into an equation $y=f(x)$ representing the calibration curve for that corresponding temperature in order to calculate the mass or concentration, or may similarly consult a lookup table representing the calibration curve. In this way, the mass estimator 260 may produce an estimate of the mass or other quantitative measure of the eluted component of interest.

The chemical analysis output interface 280 outputs one or more of the various chemical analysis outputs of the apparatus 200 for use by a downstream device or user. For example, the outputs may be stored, uploaded to a server, printed, or otherwise made available for viewing or analysis. The various outputs of the apparatus 200 include, for example, singly or in combination, an identification of one or more chemical components (e.g. an eluted component of interest) of the sample as determined by the candidate chemical identifier 240, a mass or other quantitative measure of one or more identified chemical components of the sample as estimated by the mass estimator 260, the analyzed SAW frequency response data from the SAW data analyzer 230, error reports related to failed attempts by the candidate chemical identifier 240 or mass estimator 260, etc. Such outputs may also be displayed on a screen in relation to a user query as an intermediate step in a process performed by the apparatus 200.

As noted above, the calibration curves stored in the calibration curve storage 270 may be established for specific temperatures or temperature ranges. Thus, the mass estimator 260 may reference the temperature profile stored in the temperature profile storage 215 (e.g. via the temperature profile manager 210) when comparing the peak (e.g. height or area) corresponding to the eluted component of interest to a calibration curve stored in the calibration curve storage 270. Because the peak height and area may depend on the temperature at the moment in time that the corresponding eluted component was condensed on the SAW sensor 108, the temperature profile provides a corresponding temperature for each peak that can be used to accurately estimate the mass or other quantitative measure. Along the same lines, the calibration curve builder 290 may, prior to the quantitative analysis, establish the calibration curve(s) stored in the calibration curve storage 270 in accordance with the temperature profile stored in the temperature profile storage 215. For example, a desired sensor temperature for an eluted component of interest, as indicated by the temperature profile stored in the temperature profile storage 215, may be used to build a calibration curve of the form $y=f(x)$ or in the form of a lookup table for that desired sensor temperature. The system 10 may enter a calibration mode in which standard samples containing single or multiple chemicals at known masses or concentrations are analyzed at the desired sensor temperature. After the desired number of standard samples are analyzed and the relative standard deviation (RSD) is within acceptable ranges, the relationship between mass/concentration and peak height/area is established for that temperature and may be stored in the calibration curve storage 270. In this way, it can be assured that the calibration curve storage 270 will contain calibration curve(s) associated with the relevant temperature(s) for a given analysis.

Figure 3:
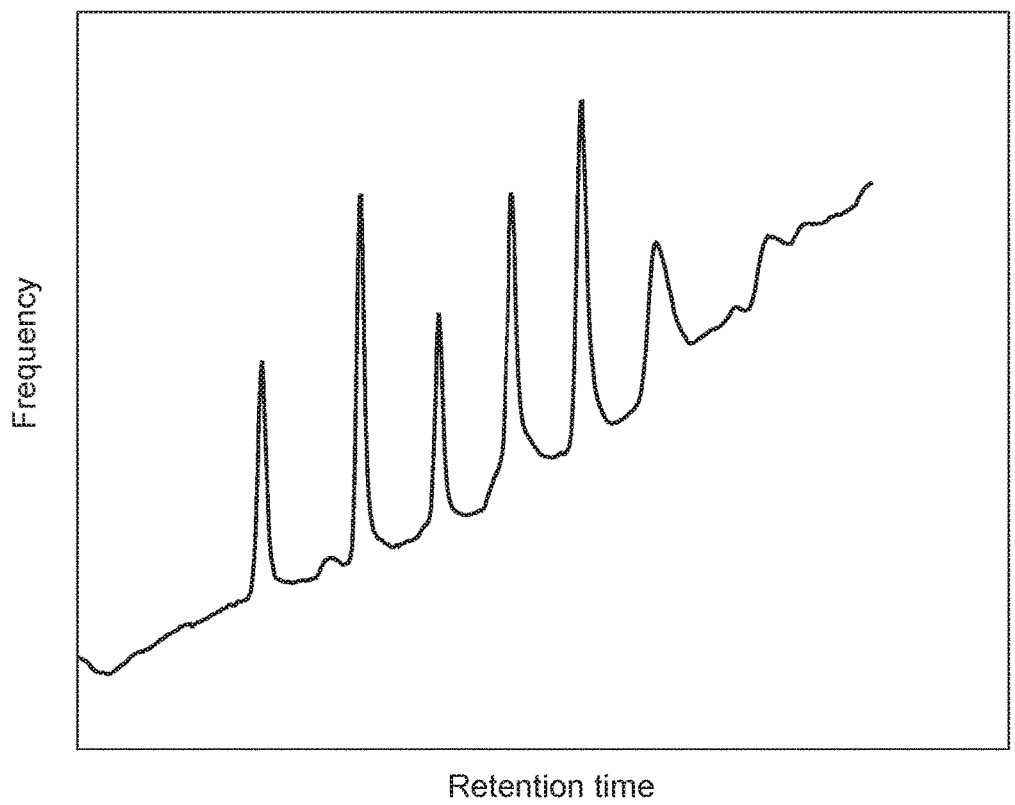
FIG. 3 is a graphical representation of an example of SAW frequency response data.

FIG. 3 is a graphical representation of an example of SAW frequency response data. As each chemical component of the sample elutes from the GC column 104, the SAW sensor 108 (or associated electronics, not shown) exhibits a SAW frequency response (shown in Hz on the y-axis) due to the accumulation of the eluted chemical component on the SAW sensor 108. The shape of each peak (e.g. height and area) is determined in part by the quantity (e.g. mass) of the component in the sample, as well as the temperature of the SAW sensor 108 in relation to the dew point of the component, which affects the width of the peak as the component accumulates on the SAW sensor 108 for a longer or shorter period of time. In addition to peaks corresponding to eluted components of interest, other peaks may correspond to other chemical components in the sample and known chemicals injected with the sample for purposes of determining retention indices (e.g. n-alkanes). SAW frequency response data like the example shown in FIG. 3 may be generated by the SAW sensor 108 or associated electronics in various forms. The SAW frequency response data need not be generated as a graphical representation as shown. Thereafter, or concurrently with its generation, the SAW frequency response data may be received by the SAW data analyzer 230 of the apparatus 200 for processing by the apparatus 200.

The example of FIG. 3 is a representation of SAW frequency response data collected at a static temperature of the SAW sensor 108. As can be seen, even at relatively earlier retention times, the peaks are asymmetric having disproportionately longer tails. As explained above, this kind of asymmetry can occur even when chemicals are captured through condensation alone. Meanwhile, at later retention times, the tails of peaks are higher than the fronts, suggesting that these chemicals were captured by further mechanisms other than condensation, such as weak Van der Waals forces and/or chemical adsorption. As the loaded chemicals cannot be released from the SAW sensor 108 under static temperature conditions, a plateau begins to form as each chemical elutes from the gas chromatograph 100. At the latest retention times, peaks begin to overlap, leading to significant uncertainty in subsequent analysis.

Figure 4:
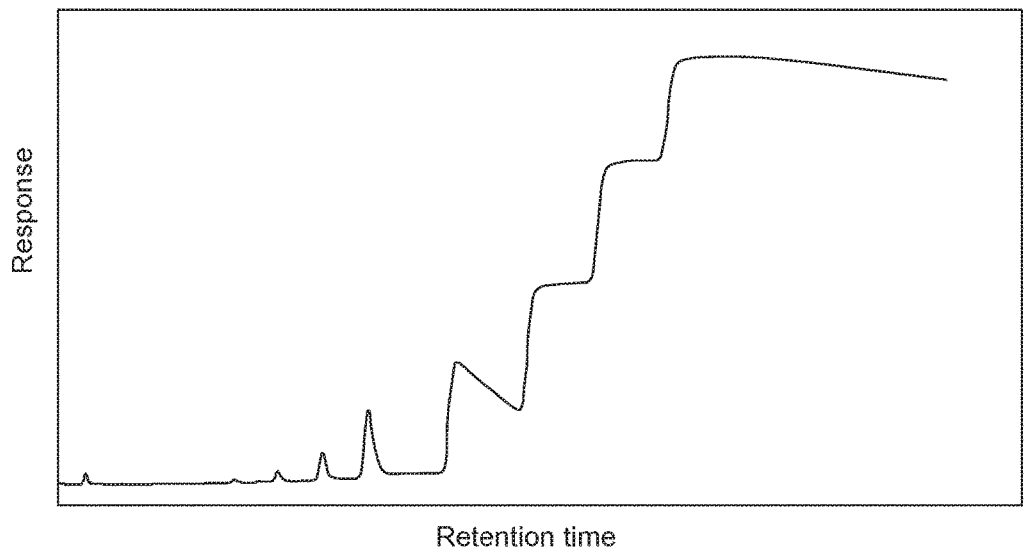
FIG. 4 is another graphical representation of an example of SAW frequency response data.

FIG. 4 is another graphical representation of an example of SAW frequency response data collected at a static temperature of the SAW sensor 108. Similar observations as made above with respect to FIG. 3 can be made with respect to FIG. 4. In FIG. 4, the plateau effect is even more pronounced as some eluted chemical components remain on the SAW sensor 108 in their entirety without being even partially released.

Figure 5:
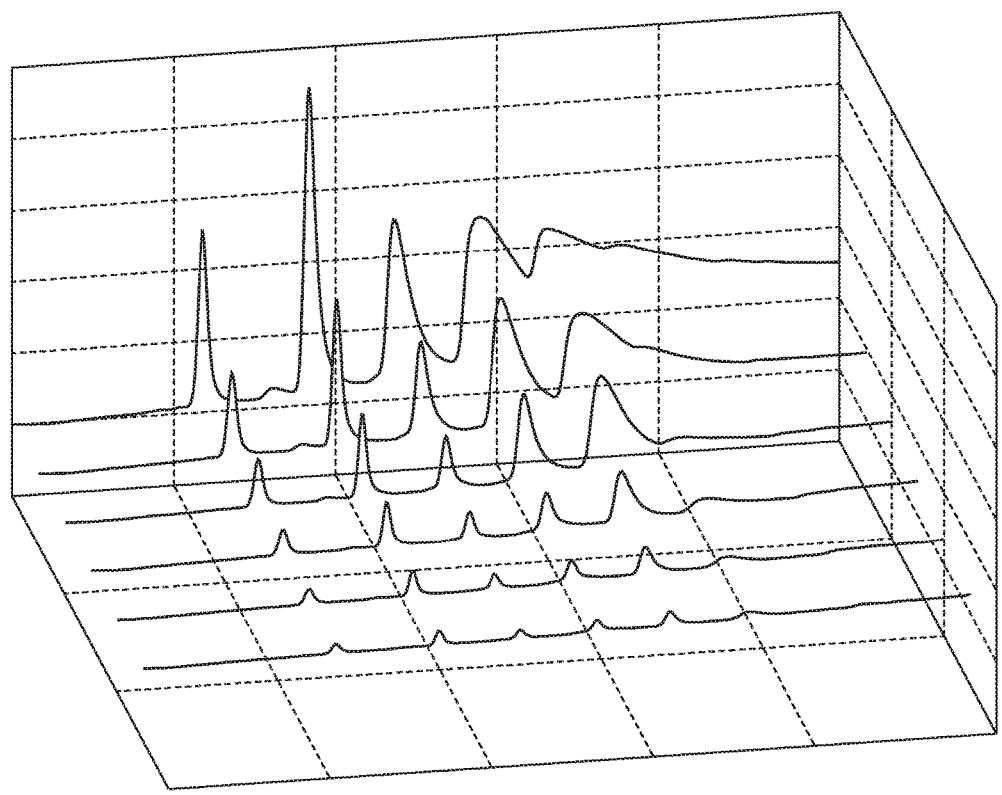
FIG. 5 is another graphical representation of an example of SAW frequency response data.

FIG. 5 is another graphical representation of an example of SAW frequency response data. In this example, the SAW sensor 108 is held at static temperature for the duration of the GC/SAW run. However, the GC/SAW run is repeated six times at progressively higher static temperatures from 10° C. to 60° C. from back to front as arranged in the plots of FIG. 5. As can be understood, the plateau effect is less for higher temperatures. This is understood to be caused by the lack of residue buildup on the SAW sensor 108 as the weak Van der Waals forces and chemical adsorption are overcome by the higher temperatures. It can also be observed that the asymmetry is less for higher temperatures, which is understood to be due to the increased temperature reducing the observable difference between condensation and evaporation kinetics. The example of FIG. 5 suggests that collecting SAW frequency response data at higher temperatures may reduce the interference between peaks and residue and avoid overlapping of peaks.

Figure 6:
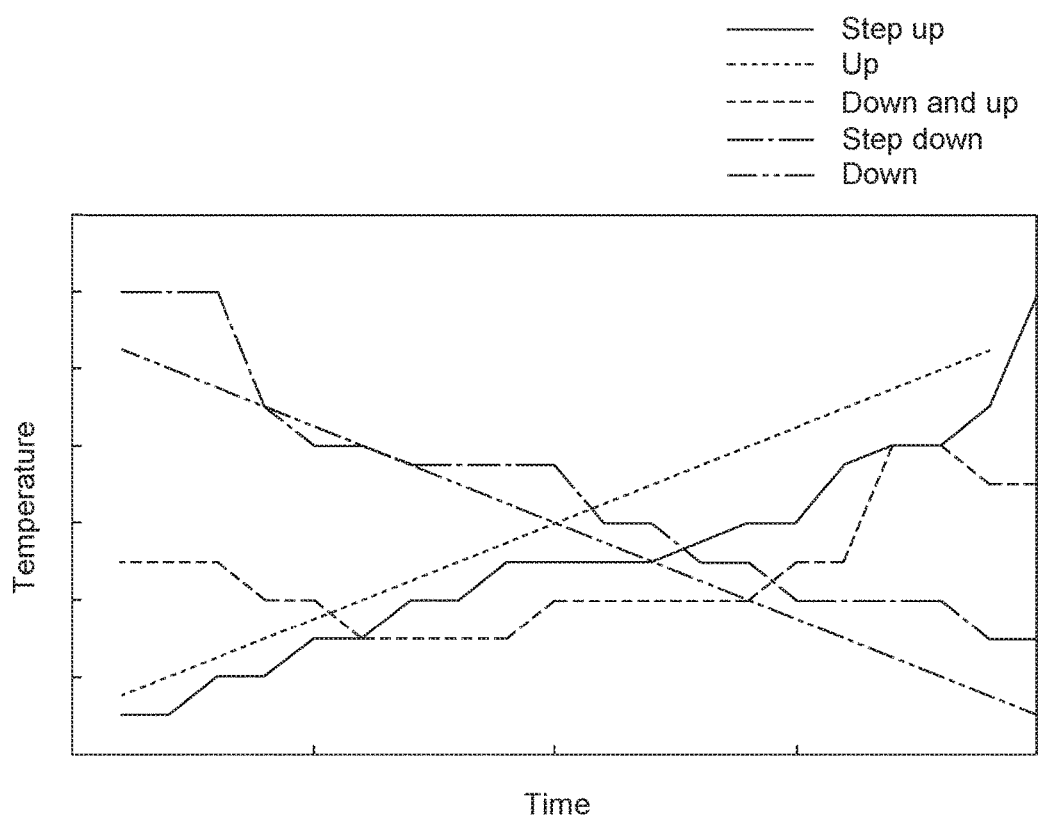
FIG. 6 shows example temperature profiles for adjusting the temperature of a SAW sensor.

FIG. 6 shows example temperature profiles for adjusting the temperature of a SAW sensor. The example temperature profiles of FIG. 6 may, for example, be used by the apparatus 200 of FIG. 2 (e.g. the temperature controller 220) to adjust the temperature of the SAW sensor 108 (see FIG. 1). In each of the five examples shown in FIG. 6, the temperature profile defines a varying target temperature (y-axis) as a function of time (x-axis), rather than a static temperature.

As shown in all of the examples of FIG. 6, the temperature profile may define the target temperature as a continuous function of time. The temperature profile may, however, define the target temperature as a discontinuous function of time, e.g. a step function. As also shown in all of the examples of FIG. 6, the temperature profile may include one or more ramp regions in which the target temperature varies linearly, though regions of non-linear temperature change are also contemplated. As shown in the "step up," "down and up," and "step down" examples of FIG. 6, the temperature profile may include two or more ramp regions in which the target temperature varies linearly, with at least two of the two or more ramp regions defining different ramp rates. As further shown in the "down and up" example of FIG. 6, the at least two ramp regions defining different ramp rates may define ramp rates with opposite sign. As shown in the "step up," "down and up," and "step down" examples of FIG. 6, the temperature profile may include two or more step regions in which the target temperature is constant, with at least two of the two or more step regions defining different target temperatures. For example, the "step up" example includes seven step regions each of which defines a different target temperature. As also shown in the "step up," "down and up," and "step down" examples of FIG. 6, the temperature profile may include two or more step regions in which the target temperature is constant, with at least two of the two or more step regions defining different step durations. For example, of the seven step regions included in the "step up" example, it appears that at least one of the step regions (the one in the middle) has a substantially longer step duration than the others.

In the following description, specific examples will be provided in which the various uses of each of the above temperature profile features (e.g. ramp regions, step regions, etc.) will become apparent. Of course, these particular features are examples only, and temperature profiles may have various other features and combinations of features that may be used to achieve various purposes in accordance with the principles described herein.

Figure 7A:
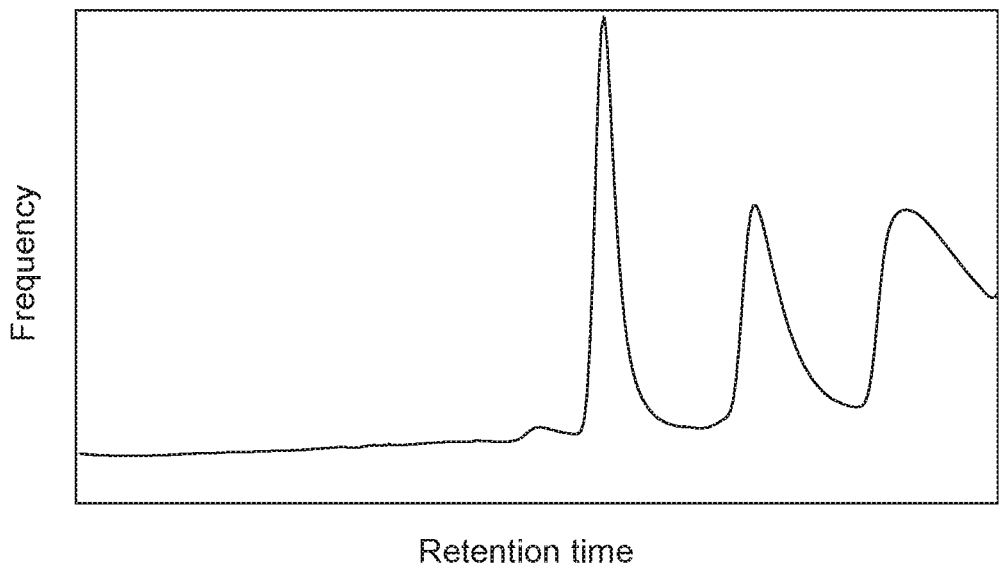
FIG. 7A is another graphical representation of an example of SAW frequency response data collected at static SAW sensor temperature.

FIG. 7A is another graphical representation of an example of SAW frequency response data collected at static SAW sensor temperature. The third of the three large peaks has a very long tail. As described above, such a long tail can detrimentally affect the analysis, for example, by hiding a subsequent peak or by causing a large quantitative error due to the distorted peak area. In accordance with the techniques described herein, a user of the apparatus 200 may immediately recognize that the latter part of the SAW frequency response data would benefit from a higher temperature to prevent unwanted mass loading on the SAW sensor 108 (e.g. by increasing the evaporation rate of condensed chemicals and/or breaking physical/chemical bonds between the chemical and the surface of the SAW sensor 108). The user may then simply create a temperature profile (or edit an existing temperature profile) using the temperature profile manager 210 and repeat the analysis run. The user may select, for example, a "step up" or "up" temperature profile (see FIG. 6) with specific parameters suited to the SAW frequency response data shown in FIG. 7A. As an example, the user may create a temperature profile having two step regions: a first step region defining a first, unchanged (e.g. default) temperature from the beginning of the run until a time shortly after the retention time of the second peak and a second step region defining a second, elevated temperature thereafter. Between the first and second step regions, the user may define a linear ramp region. Non-linear regions and discontinuities are also possible, as noted above.

Figure 7B:
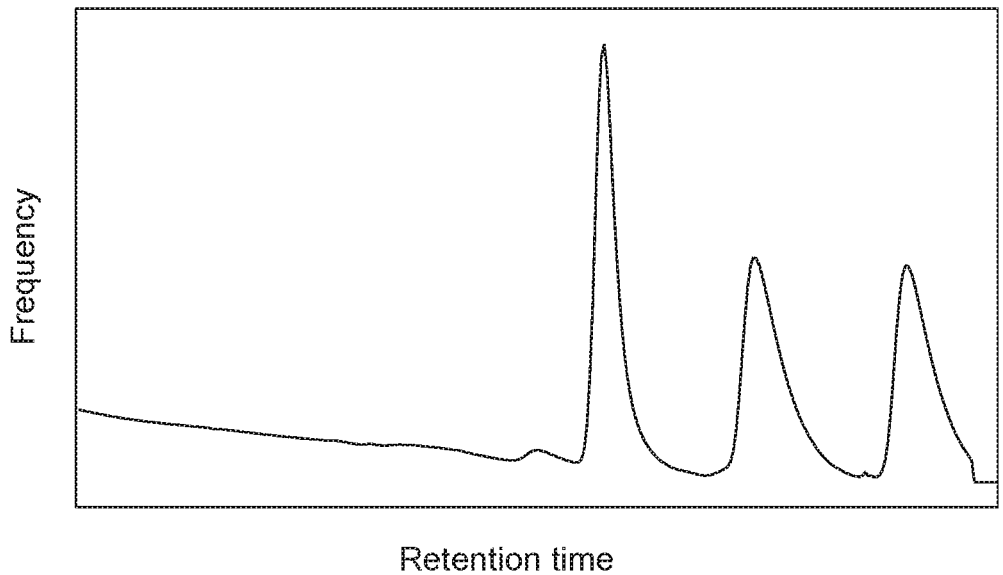
FIG. 7B is a graphical representation of SAW frequency response data similar to that of FIG. 7A but with temperature control according to an embodiment of the present disclosure.

FIG. 7B is a graphical representation of SAW frequency response data similar to that of FIG. 7A, but with temperature control according to an embodiment of the present disclosure. Due to the control of the thermoelectric cooler 112 by the apparatus 200 in accordance with a temperature profile that selectively increases the temperature in the latter part of the analysis run, the third peak no longer exhibits the long tail of FIG. 7A. As a result, quantitative analysis of the eluted chemical component associated with the third peak can be more accurately achieved, e.g. by the mass estimator 260 of the apparatus 200. In addition, it can now be confirmed that there is no hidden peak immediately after the third peak, which might have been hidden in the long tail of FIG. 7A.

Figure 8A:
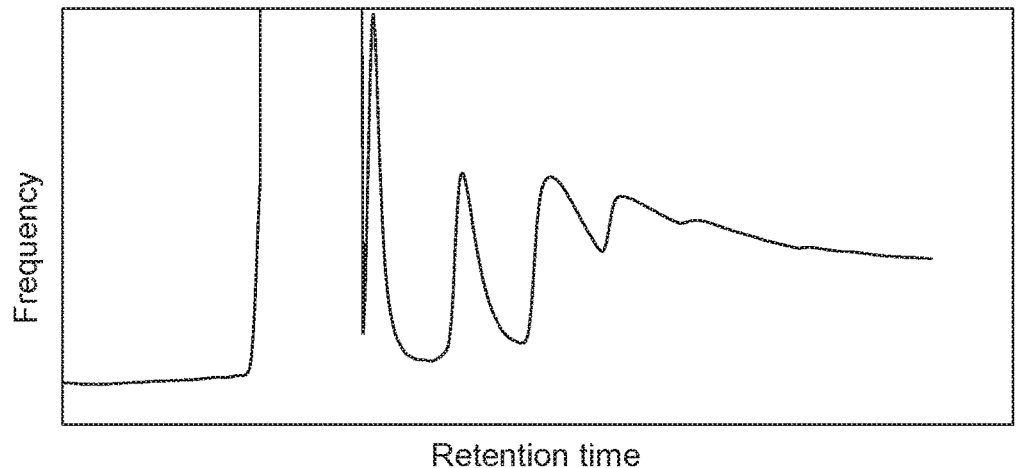
FIG. 8A is another graphical representation of an example of SAW frequency response data collected at static SAW sensor temperature.

FIG. 8A is another graphical representation of an example of SAW frequency response data collected at static SAW sensor temperature. A saturated region exists at the beginning of the analysis, due to the mass loading of the SAW sensor 108 being so high that the oscillation frequency reduces to a very low level that cannot be reported accurately. As described above, such a saturation peak may take an extended duration to disappear and may make detection of subsequently eluted chemical components difficult or impossible. In this case, the existence of the saturation peak makes it unclear where the next peak begins, making quantitative analysis difficult. In accordance with the techniques described herein, a user of the apparatus 200 may immediately recognize that the beginning part of the SAW frequency response data would benefit from a higher temperature to prevent unwanted mass loading on the SAW sensor 108. For the sake of this example, the user may also know ahead of time that there are no interesting peaks in the saturation region and may only be interested in cleaning up the immediately subsequent peak for a more accurate quantitative analysis. The user may not be interested in short retention time or high concentration chemicals known to be present in the sample.

The user may therefore select, for example, a "step down" or "down" temperature profile (see FIG. 6) with specific parameters suited to the SAW frequency response data shown in FIG. 8A. As an example, the user may create a temperature profile having two step regions: a first step region defining a first, elevated temperature from the beginning of the run until a time in the middle of the saturation peak and a second step region defining a second, unchanged (default) temperature thereafter. The saturation peak may be due to a large amount of mass loading at the beginning of the saturation peak, with a lasting effect extending for the duration of the saturation peak. Therefore, in order to remove the saturation peak, it may not be necessary for the temperature profile to remain at the first step region for long. The user may, for example, choose a halfway point of the saturation peak as the timing at which the first step region should end or as the timing at which the second step region should begin. Adjustments can then be made as necessary after a subsequent analysis run.

Figure 8B:
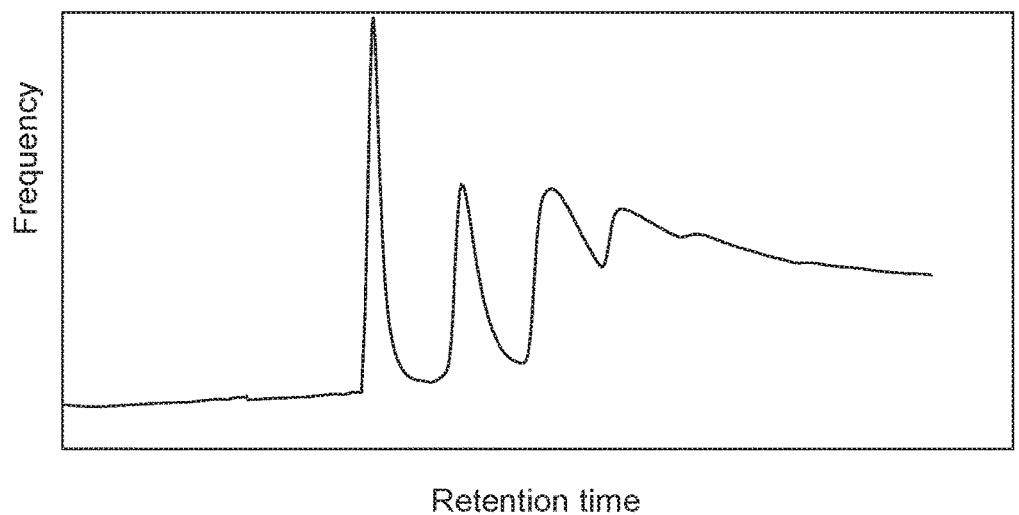
FIG. 8B is a graphical representation of SAW frequency response data similar to that of FIG. 8A but with temperature control according to an embodiment of the present disclosure.

FIG. 8B is a graphical representation of SAW frequency response data similar to that of FIG. 8A but with temperature control according to an embodiment of the present disclosure. Due to the control of the thermoelectric cooler 112 by the apparatus 200 in accordance with a temperature profile that selectively increases the temperature in the beginning part of the analysis run, the saturation peak of FIG. 8A has been successfully removed. As a result, quantitative analysis of the eluted chemical component associated with the subsequent peak (the first peak in FIG. 8) can be more accurately achieved, e.g. by the mass estimator 260 of the apparatus 200. In this particular example, the user was only interested in the peak immediately subsequent to the saturation peak. If later peaks had also been of interest, the user may have used a "down and up" temperature profile in order to ramp up the temperature toward the end of the analysis and correct for the plateau that begins to appear in the last few peaks.

Figure 9A:
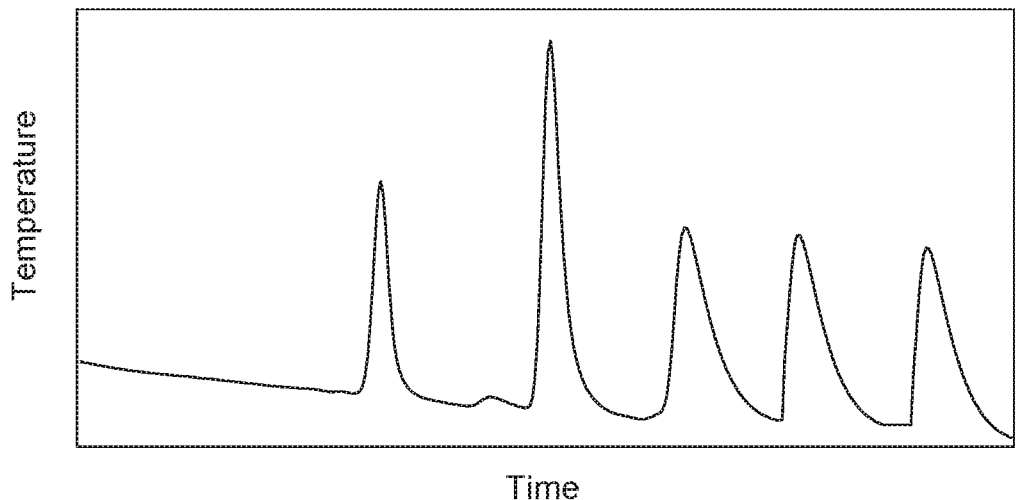
FIG. 9A is another graphical representation of an example of SAW frequency response data collected at static SAW sensor temperature.

FIG. 9A is another graphical representation of an example of SAW frequency response data collected at static SAW sensor temperature. Of the five peaks shown, the user of the apparatus 200 may be uninterested in one or more of the peaks. In accordance with the techniques described herein, the user may eliminate any peak that is uninteresting, even if it is in the middle of the analysis run, thereby simplifying the analysis and reducing interference from unwanted chemicals. In this case, the user may be uninterested in the third peak of the five peaks. The user may therefore select, for example, a "down and up" temperature profile (see FIG. 6) with specific parameters suited to the SAW frequency response data shown in FIG. 9A. As an example, the user may create a temperature profile having three step regions: a first step region defining a first, unchanged (e.g. default) temperature from the beginning of the run until a time shortly after the retention time of the second peak, a second step region defining a second, elevated temperature until a time shortly after the retention time of the third, unwanted peak, and a third step region again defining the first, unchanged (e.g. default) temperature for the remainder of the analysis run. (In this case, the "down and up" temperature profile might be referred to as "up and down.") Alternatively, the temperature profile may have only two step regions separated by a pair of ramp regions momentarily ramping the temperature up and down at the time of the third, unwanted peak (i.e. with no appreciable step region at the elevated temperature).

Figure 9B:
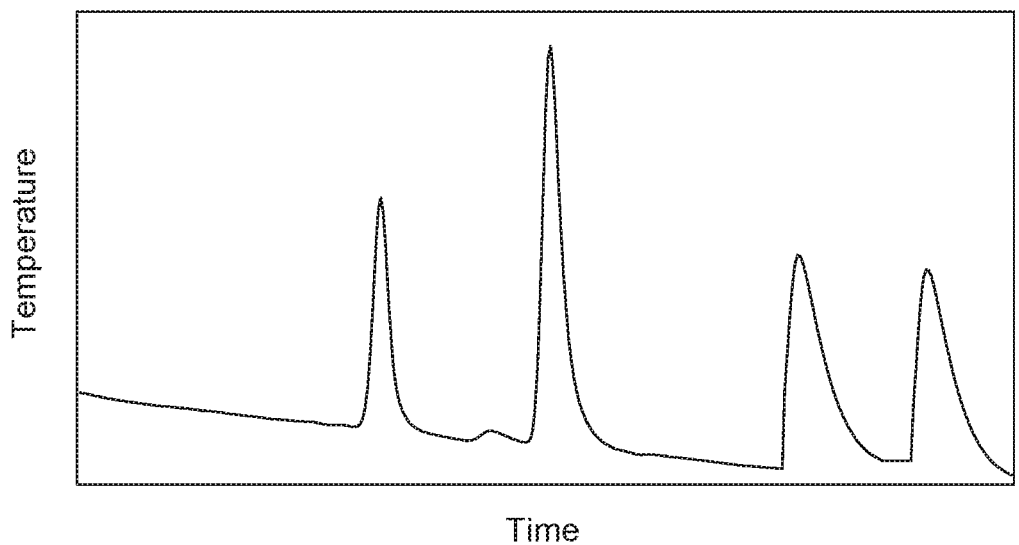
FIG. 9B is a graphical representation of SAW frequency response data similar to that of FIG. 9A but with temperature control according to an embodiment of the present disclosure.

FIG. 9B is a graphical representation of SAW frequency response data similar to that of FIG. 9A but with temperature control according to an embodiment of the present disclosure. Due to the control of the thermoelectric cooler 112 by the apparatus 200 in accordance with a temperature profile that selectively increases the temperature around the retention time of the third, unwanted peak, the third peak of FIG. 9A has been successfully removed. As a result, the SAW frequency response data can be simplified for subsequent analysis by the apparatus 200 (e.g. by the SAW data analyzer 230) and any interference with adjacent peaks caused by the unwanted peak can be reduced, resulting in faster and more accurate quantitative analysis of the eluted chemical components of interest.

Figure 10A:
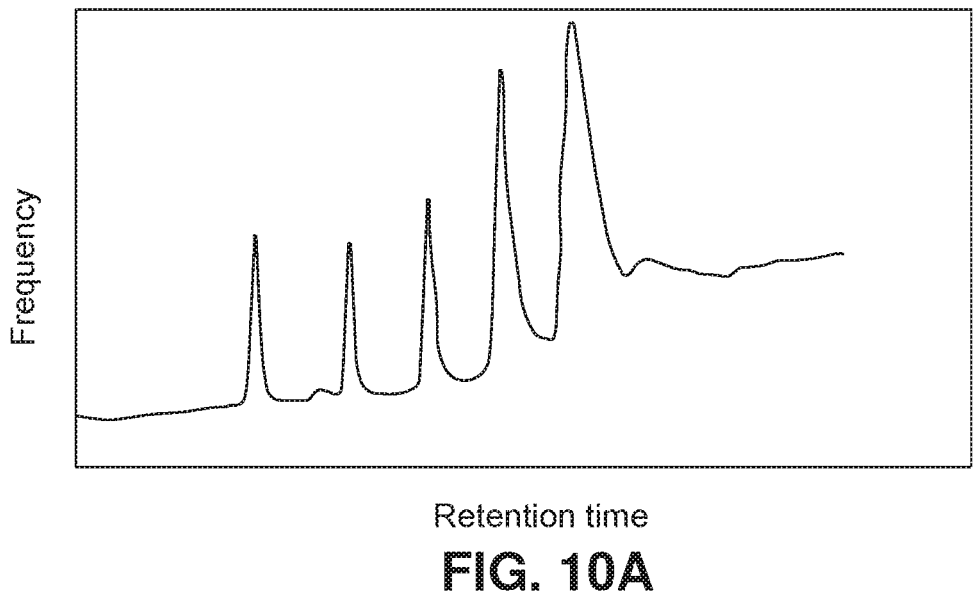
FIG. 10A is another graphical representation of an example of SAW frequency response data collected at static SAW sensor temperature.

FIG. 10A is another graphical representation of an example of SAW frequency response data collected at static SAW sensor temperature. Of the five peaks shown, the user of the apparatus 200 may be particularly interested in one or more of the peaks. In accordance with the techniques described herein, the user may enhance any peak that is particularly interesting, even if it is in the middle of the analysis run, thereby improving the detection capability of the system 10 for that peak. In this case, the user may be particularly interested in the second peak of the five peaks. The user may therefore select, for example, a "down and up" temperature profile (see FIG. 6) with specific parameters suited to the SAW frequency response data shown in FIG. 10A. As an example, the user may create a temperature profile having three step regions: a first step region defining a first, unchanged (e.g. default) temperature from the beginning of the run until a time shortly after the retention time of the first peak, a second step region defining a second, reduced temperature until a time shortly after the retention time of the second, particularly interesting peak, and a third step region again defining the first, unchanged (e.g. default) temperature for the remainder of the analysis run. Alternatively, the temperature profile may have only two step regions separated by a pair of ramp regions momentarily ramping the temperature down and up at the time of the second, particularly interesting peak (i.e. with no appreciable step region at the reduced temperature).

Figure 10B:
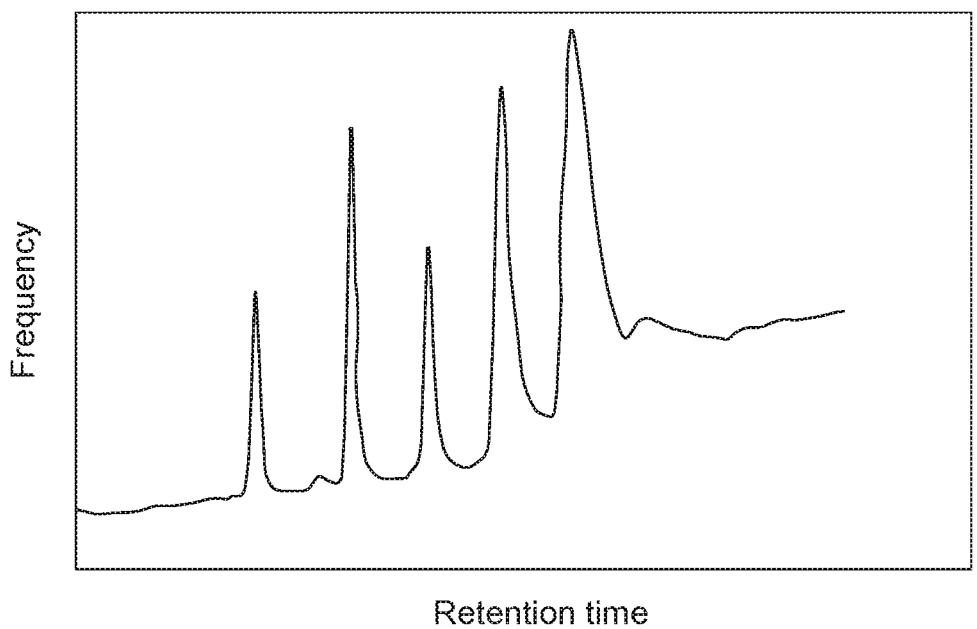
FIG. 10B is a graphical representation of SAW frequency response data similar to that of FIG. 10A but with temperature control according to an embodiment of the present disclosure.

FIG. 10B is a graphical representation of SAW frequency response data similar to that of FIG. 10A but with temperature control according to an embodiment of the present disclosure. Due to the control of the thermoelectric cooler 112 by the apparatus 200 in accordance with a temperature profile that selectively decreases the temperature around the retention time of the second, particularly interesting peak, the second peak of FIG. 10A has been successfully enhanced without altering the other peaks of the SAW frequency response data. As a result, the detection capability of the system 10 for that peak can be improved because more of the chemical component of interest was allowed to condense and remain condensed due to the reduced temperature, as evidenced by a larger peak. The improved detection capability may include, for example, an improved resolution or accuracy of the SAW data analyzer 230 in characterizing the peak by a GC retention time, resulting in more accurate qualitative analysis by the candidate chemical identifier 240. As another example, the improved detection capability may include an improved resolution or accuracy of the SAW data analyzer 230 in characterizing the peak by a peak height and/or a peak area, which may result in more accurate quantitative analysis by the mass estimator 260.

Figure 11:
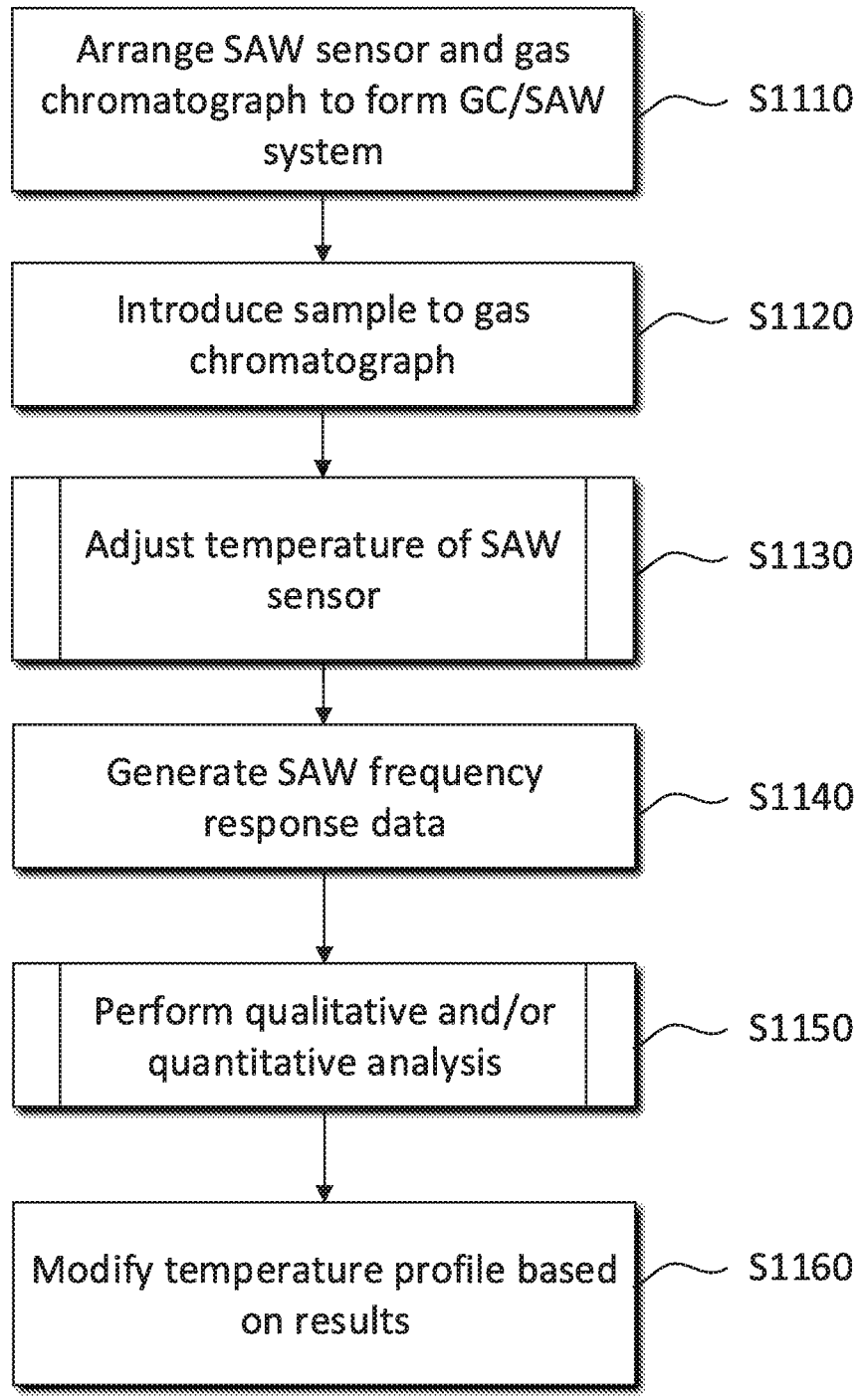
FIG. 11 is an example operational flow in relation to the system shown in FIG. 1 according to an embodiment of the present disclosure.

FIG. 11 is an example operational flow in relation to the system 10 shown in FIG. 1 according to an embodiment of the present disclosure. First, the SAW sensor 108 and the gas chromatograph 100 are arranged to form a GC/SAW system such that eluted components separated from the sample by the gas chromatograph 100 accumulate at a condensation spot 110 on the SAW sensor 108 (S1110). Once the GC/SAW system is set up, a sample is introduced into the gas chromatograph 100 (S1120). As chemical components elute from the GC column 104, the temperature of the SAW sensor 108 is adjusted according to a temperature profile (S1130) and SAW frequency response data is generated by the SAW sensor 108 or associated electronics (S1140). For example, the temperature controller 220 of the apparatus 200 may adjust the temperature of the SAW sensor 108 according to a temperature profile stored in the temperature profile storage 215 and accessed via the temperature profile manager 210. In an initial analysis run, the temperature profile may be a default temperature profile, such as a static temperature profile. In such case, adjusting the temperature of the SAW sensor 108 may refer to controlling the temperature to remain unchanged or simply leaving the temperature unchanged from a default setting of the thermoelectric cooler 112.

After the SAW frequency response data is generated, qualitative and/or quantitative analysis is performed (S1150). For example, the SAW frequency response data may be received by the apparatus 200 (e.g. transferred by a data storage medium or transferred by a wired or wireless connection, either locally or remotely) and the apparatus 200 may determine the identity of one or more chemical components of interest using the candidate chemical identifier 240 and/or estimate the mass or other quantitative measure of one or more chemical components of interest using the mass estimator 260. Lastly, the temperature profile is modified as necessary or desired based on the results of the qualitative and/or quantitative analysis (S1160). For example, a user of the apparatus 200 may use the temperature profile manager 210 to modify the temperature profile stored in the temperature profile storage 215 as described in relation to FIGS. 6-10B upon observing a chromatogram of the SAW frequency response data like the examples in FIG. 7A, 8A, 9A, or 10A. The chromatogram may be one of the outputs of the chemical analysis output interface 280, and the user may observe the chromatogram and manually edit the temperature profile using the temperature profile manager 210 in accordance with the particular goals of the analysis. Other parameter(s) of the setup configuration of the system 10 of FIG. 1 may also be adjusted based on the results of the apparatus 200 and/or automatically by the apparatus 200.

In addition to manual editing of the temperature profile, it is also contemplated that the temperature profile manager 210 may automatically modify the temperature profile in accordance with preprogrammed instructions. For example, the temperature profile manager 210 may be programmed with an expected peak count or an expected peak size. On the basis of such preprogrammed instructions and the receipt of peak characterization output of the SAW data analyzer 230 (e.g. retention time, peak height, or peak area derived from SAW frequency response data), the temperature profile manager 210 may automatically modify the temperature profile to increase peak count or peak size (by reducing the temperature) or to decrease peak count or peak size (by elevating the temperature) in order to achieve the expected peak count in a subsequent analysis run. Preprogramming for such automatic control may further include an expected peak count or an expected peak size at a particular retention time or range of retention times, or may include expected peak positions (i.e. expected retention times). Accordingly, the temperature profile manager 210 might modify the temperature profile to include time dependence as shown in FIG. 6.

Figure 12:
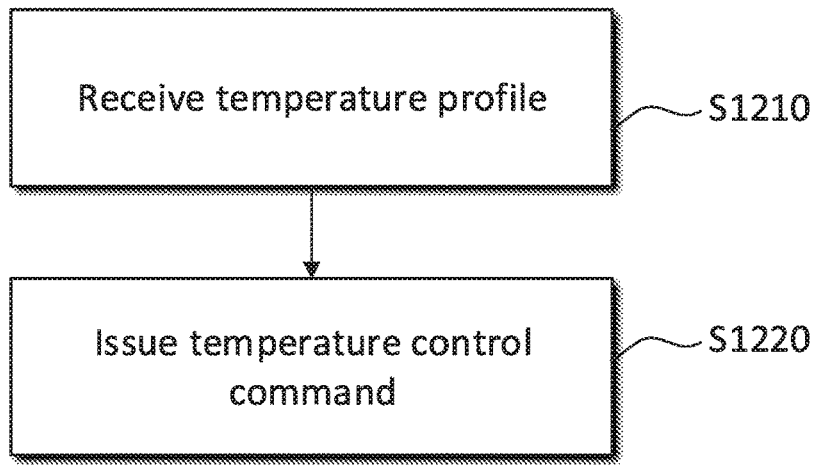
FIG. 12 is an example operational flow of step S1130 in FIG. 11.

FIG. 12 is an example operational flow of step S1130 in FIG. 11. As noted above, the temperature controller 220 of the apparatus 200 may adjust the temperature of the SAW sensor 108 according to a temperature profile stored in the temperature profile storage 215 and accessed via the temperature profile manager 210. More specifically, the temperature profile manager 210 of the apparatus 200 may receive a temperature profile from outside the apparatus 200 as temperature profile data or as a series of user input commands for creating the temperature profile from scratch or modifying an existing temperature profile (S1210). In the case of automatic modifying of the temperature profile as described above, the temperature profile manager 210 may be regarded as receiving the modified temperature profile from the automatic editing functionality of the temperature profile manager 210. The temperature profile may then be provided to the temperature controller 220 and stored in the temperature profile storage 215 (e.g. for later editing). On the basis of the temperature profile, the temperature controller 220 may define a time-varying temperature set point. As the GC/SAW system proceeds with the analysis of the sample, the temperature controller 220 may issue temperature control commands to the thermoelectric cooler 112 as a function of the set point defined by the temperature profile and a feedback signal received from the thermoelectric cooler 112 as described above (S1220).

Figure 13:
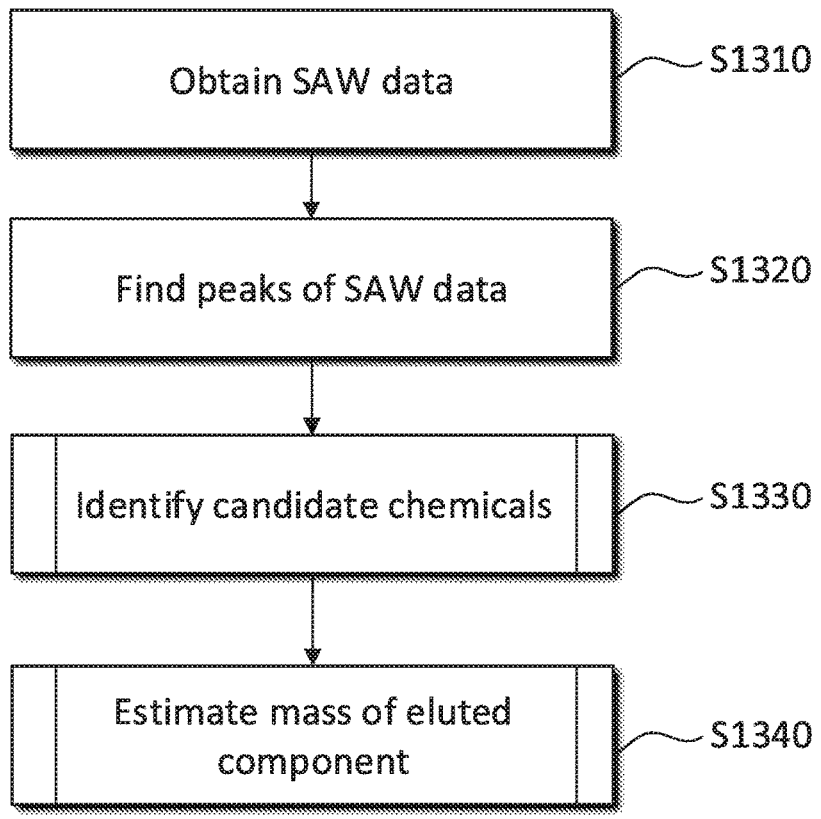
FIG. 13 is an example operational flow of step S1140 in FIG. 11.

FIG. 13 is an example operational flow of step S1140 in FIG. 11. First, the apparatus 200 receives SAW frequency response data (S1310). For example, the SAW data analyzer 230 of the apparatus 200 may receive SAW frequency response data generated by the SAW sensor 108 or associated electronics as described above. That is, the SAW data analyzer 230 may receive SAW frequency response data generated by the SAW sensor 108 of the GC/SAW system shown in FIG. 1, the SAW frequency response data including one or more peaks corresponding respectively to one or more eluted components separated from a sample by the gas chromatograph 100. The SAW data analyzer 230 may, as part of receiving the data, align, trim, interpolate, reformat, etc. the data for use by the apparatus 200.

Having received the SAW frequency response data, the apparatus 200 identifies peaks and valleys of the SAW data (S1320). For example, the SAW data analyzer 230 of the apparatus 200 may identify the one or more peaks of the SAW frequency response data corresponding to the eluted components and may further identify one or more valleys of the SAW frequency response data by any known method as described above. For each of the found peaks or some subset thereof, the apparatus 200 identifies a set of one or more candidate chemicals (S1330). For example, the candidate chemical identifier 240 of the apparatus 200 may identify a set of one or more candidate chemicals for an eluted component of interest based on the corresponding peak of the SAW frequency response data as characterized by the SAW data analyzer 230. Lastly, the apparatus 200 may estimate the mass or other quantitative measure of the eluted component of interest (S1340). For example, the mass estimator 260 of the apparatus 200 may estimate the mass or other quantitative measure by comparing the corresponding peak of the SAW frequency response data to a calibration curve stored in the calibration curve storage 270.

Figure 14:
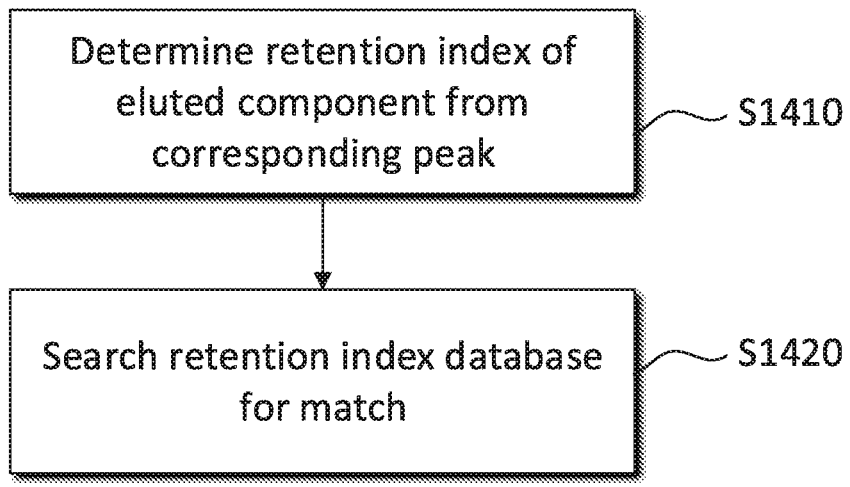
FIG. 14 is an example operational flow of step S1330 in FIG. 13.

FIG. 14 is an example operational flow of step S1330 in FIG. 13. For a given peak of the SAW frequency response data, the apparatus 200 may identify a set of one or more candidate chemicals using a retention index. For example, the retention index calculator 242 of the candidate chemical identifier 240 may calculate a retention index of the eluted component from the corresponding peak (S1410). Then, the retention index search engine 244 may search the retention index database 250 for one or more matches between the determined retention index and chemicals in the retention index (S1420). In this way, the set of one or more candidate chemicals for the peak may consist of each matched chemical in the retention index database 250, e.g. each known chemical having substantially the same retention index as the determined retention index or having retention indices within a predetermined error range of the determined retention index.

Figure 15:
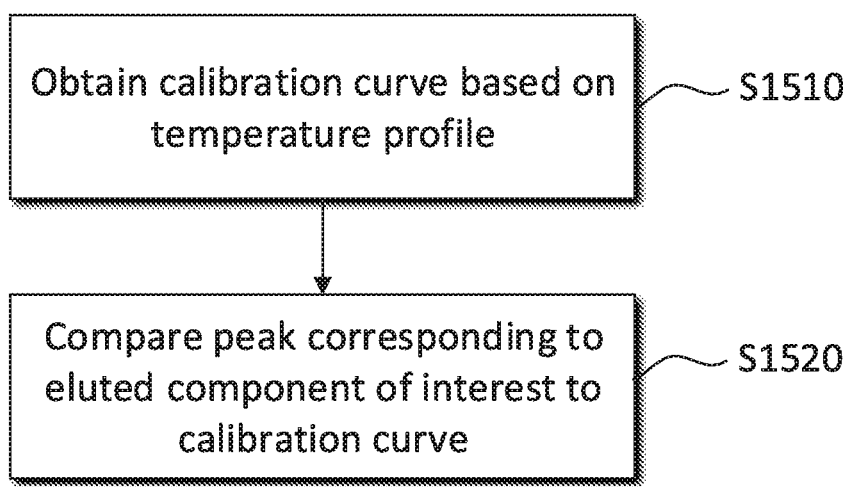
FIG. 15 is an example operational flow of step S1340 in FIG. 13.

FIG. 15 is an example operational flow of step S1340 in FIG. 13. As noted above, the calibration curves stored in the calibration curve storage 270 may be established for specific temperatures or temperature ranges. The apparatus 200 may thus obtain an appropriate calibration curve based on the temperature profile stored in the temperature profile storage 215 (S1510). Obtaining the calibration curve may include, for example, the mass estimator 260 of the apparatus 200 choosing a calibration curve from the calibration curve storage 270 with reference to the temperature profile stored in the temperature profile storage 215. Instead, or additionally, obtaining the calibration curve may include the calibration curve builder 290 establishing an appropriate calibration curve for storage in the calibration curve storage 270 based on the temperature profile stored in the temperature profile storage 215. With an appropriate calibration curve thus obtained for a given peak corresponding to an eluted component of interest, the mass estimator 260 then compares the peak (e.g. height or area) to the calibration curve to produce an estimate of the mass or other quantitative measure of the eluted component of interest (S1520).

By using the systems, methods, and apparatuses described herein, it is possible to selectively adjust the temperature of a SAW sensor in a GC/SAW system to compensate for unwanted mass buildup on a SAW sensor. For example, asymmetric peaks, saturation peaks, and plateaus in the SAW frequency response data can be corrected by selectively increasing the temperature using a time-dependent temperature profile to reverse condensation and/or physical/chemical adsorption on the SAW sensor. In this way, hidden peaks may be revealed and the accuracy of the quantitative analysis may be improved. Selective removal of uninteresting peaks and emphasis or enhancement of particularly interesting peaks is also possible using the temperature profile, allowing for simplified analysis and improved detection capability. Because the systems, methods, and apparatuses described herein can improve the effectiveness of using the SAW frequency response data to identifying chemicals, the requirements of the GC/SAW system can be relaxed, with the size of the instrument and cost of operation being reduced accordingly.

Figure 16A:
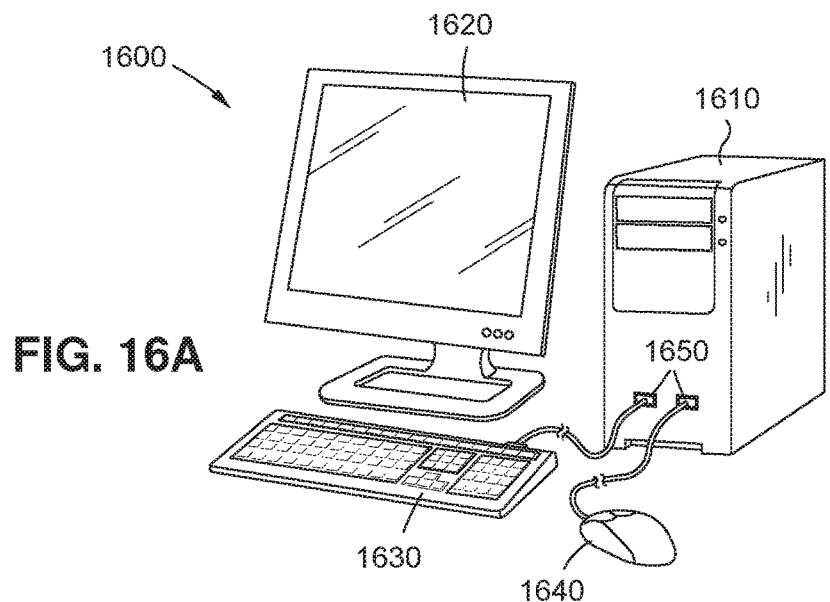
FIGS. 16A and 16B show an example of a computer in which the apparatus of FIG. 2, the operational flows of FIGS. 11-15, and/or other embodiments of the claimed invention may be wholly or partly embodied, with FIG. 16A showing a computer and FIG. 16B showing a block diagram of a system unit.
Figure 16B:
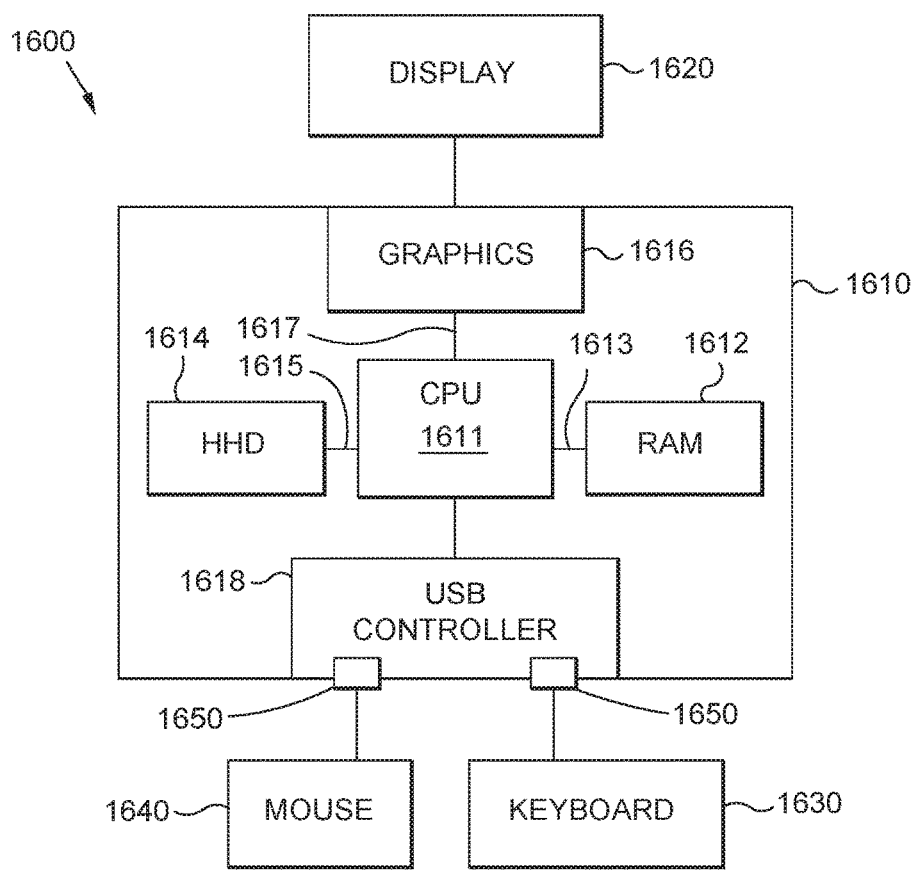

FIGS. 16A and 16B show an example of a computer 1600 in which the apparatus 200 of FIG. 2, the operational flows of FIGS. 11-15, and/or other embodiments of the claimed invention may be wholly or partly embodied. The computer 1600 according to the present embodiment, as shown in FIG. 16A, generally includes a system unit 1610 and a display device 1620. The display device 1620 produces a graphical output from the data processing operations performed by the system unit 1610. Input devices including a keyboard 1630 and a mouse 1640, for example, may be manipulated by a user to generate corresponding inputs to the data processing operations, and are connected to the system unit 1610 via ports 1650. Various other input and output devices may be connected to the system unit 1610, and different interconnection modalities are known in the art.

As shown in the block diagram of FIG. 16B, the system unit 1610 includes a processor (CPU) 1611, which may be any conventional type. A system memory (RAM) 1612 temporarily stores results of the data processing operations performed by the CPU 1611, and is interconnected thereto typically via a dedicated memory channel 1613. The system unit 1610 may also include permanent storage devices such as a hard drive 1614, which is also in communication with the CPU 1611 over an input/output (I/O) bus 1615. A dedicated graphics module 1616 may also connected to the CPU 1611 via a video bus 1617, and transmits signals representative of display data to the display device 1620. As indicated above, the keyboard 1630 and the mouse 1640 are connected to the system unit 1610 over the ports 1650. In embodiments where the ports 1650 are Universal Serial Bus (USB) type, there may be a USB controller 1618 that translates data and instructions to and from the CPU 1611 for the external peripherals connected via the ports 1650 or wirelessly connected such as via Bluetooth connectivity. Additional devices such as printers, microphones, speakers, and the like may be connected to the system unit 1610 thereby.

The system unit 1610 may utilize any operating system having a graphical user interface (GUI), such as WINDOWS from Microsoft Corporation of Redmond, Wash., MAC OS from Apple, Inc. of Cupertino, Calif., various versions of UNIX with the X-Windows windowing system, and so forth. The system unit 1610 executes one or more computer programs, with the results thereof being displayed on the display device 1620. Generally, the operating system and the computer programs are tangibly embodied in a computer-readable medium, e.g., the hard drive 1614. Both the operating system and the computer programs may be loaded from the aforementioned data storage devices into the RAM 1612 for execution by the CPU 1611. The computer programs may comprise instructions, which, when read and executed by the CPU 1611, cause the same to perform or execute the steps or features of the various embodiments set forth in the present disclosure.

For example, a program that is installed in the computer 1600 can cause the computer 1600 to function as an apparatus such as the apparatus 200 of FIG. 2. Such a program may act on the CPU 1611 to cause the computer 1600 to function as some or all of the sections, components, elements, databases, engines, interfaces, etc. of the apparatus 200 of FIG. 2 (e.g., the temperature profile manager 210, the candidate chemical identifier 240, etc.). A program that is installed in the computer 1600 can also cause the computer 1600 to perform an operational flow such as those illustrated in FIG. 11-15 or a portion thereof. Such a program may, for example, act on the CPU 1611 to cause the computer 1600 to perform one or more of the steps of FIG. 11 (e.g., adjust temperature of SAW sensor S1130, perform qualitative and/or quantitative analysis S1150, etc.).

The above-mentioned program may be provided to the hard drive 1614 by or otherwise reside on an external storage medium such as a DVD-ROM, optical recording media such as a Blu-ray Disk or a CD, magneto-optic recording medium such as an MO, a tape medium, a semiconductor memory such as an IC card, a mechanically encoded medium such as a punch card, etc. Additionally, program storage media can include a hard disk or RAM in a server system connected to a communication network such as a dedicated network or the Internet, such that the program may be provided to the computer 1600 via the network. Program storage media may, in some embodiments, be non-transitory, thus excluding transitory signals per se, such as radio waves or other electromagnetic waves.

Instructions stored on a program storage medium may include, in addition to code executable by a processor, state information for execution by programmable circuitry such as a field-programmable gate arrays (FPGA) or programmable logic array (PLA).

Although certain features of the present disclosure are described in relation to a computer 1600 with input and output capabilities including a keyboard 1630 and mouse 1640, specifics thereof are presented by way of example only and not of limitation. Any alternative graphical user interfaces such as touch interfaces and pen/digitizer interfaces may be substituted. The analogs of those features will be readily appreciated, along with suitable modifications to accommodate these alternative interfaces while still achieving the same functionalities.

Along these lines, the foregoing computer 1600 represents only one exemplary apparatus of many otherwise suitable for implementing aspects of the present disclosure, and only the most basic of the components thereof have been described. It is to be understood that the computer 1600 may include additional components not described herein, and may have different configurations and architectures. Any such alternative is deemed to be within the scope of the present disclosure.

The above description is given by way of example, and not limitation. Given the above disclosure, one skilled in the art could devise variations that are within the scope and spirit of the innovations disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for identification of chemicals in a sample, the method comprising:
   receiving a temperature profile defining a varying target temperature as a function of time;
   separating one or more eluted components from a sample with a gas chromatograph;
   adjusting a temperature of a surface acoustic wave sensor in accordance with the temperature profile as the one or more eluted components are separated from the sample by the gas chromatograph, the surface acoustic wave sensor being coupled with the gas chromatograph to define a gas chromatography/surface acoustic wave system, the one or more eluted components being separated from the sample by the gas chromatograph accumulate at a condensation spot on the surface acoustic wave sensor;
   generating surface acoustic wave frequency response data with the surface acoustic wave sensor, the surface acoustic wave frequency response data including one or more peaks corresponding respectively to the one or more eluted components separated from the sample by the gas chromatograph; and
   identifying a set of one or more candidate chemicals for an eluted component of interest based on a corresponding peak of the surface acoustic wave frequency response data.

2. The method of claim 1, wherein the temperature profile defines the target temperature as a continuous function of time.

3. The method of claim 1, wherein the temperature profile includes one or more ramp regions in which the target temperature varies linearly.

4. The method of claim 3, wherein the temperature profile includes two or more ramp regions in which the target temperature varies linearly, at least two of the two or more ramp regions defining different ramp rates.

5. The method of claim 4, wherein the at least two of the two or more ramp regions define ramp rates with opposite sign.

6. The method of claim 1, wherein the temperature profile includes one or more step regions in which the target temperature is constant.

7. The method of claim 6, wherein the temperature profile includes two or more step regions in which the target temperature is constant, at least two of the two or more step regions defining different target temperatures.

8. The method of claim 6, wherein the temperature profile includes two or more step regions in which the target temperature is constant, at least two of the two or more step regions defining different step durations.

9. The method of claim 1, further comprising:
calculating a retention index for the eluted component of interest from the corresponding peak of the surface acoustic wave frequency response data;
wherein said identifying the set of one or more candidate chemicals for the eluted component of interest includes searching a retention index database for one or more matches between the calculated retention index and chemicals in the retention index database.

10. The method of claim 1, further comprising:
estimating a mass of the eluted component of interest based on the corresponding peak of the surface acoustic wave frequency response data.

11. The method of claim 10, wherein said estimating the mass includes comparing the peak corresponding to the eluted component of interest to a calibration curve.

12. The method of claim 11, further comprising:
establishing the calibration curve in accordance with the temperature profile.

13. The method of claim 1, further comprising:
modifying the temperature profile based upon a result of the identifying.

14. A system for identification of chemicals in a sample, the system comprising:
a gas chromatograph;
a surface acoustic wave sensor coupled with the gas chromatograph to define a gas chromatography/surface acoustic wave system in which one or more eluted components separated from a sample by the gas chromatograph accumulate at a condensation spot on the surface acoustic wave sensor, the surface acoustic wave sensor generating surface acoustic wave frequency response data including one or more peaks corresponding respectively to the one or more eluted components separated from the sample by the gas chromatograph;
a thermoelectric cooler operable to adjust a temperature of the surface acoustic wave sensor;
a temperature controller that receives a temperature profile defining a varying target temperature as a function of time and instructs the thermoelectric cooler to adjust the temperature of the surface acoustic wave sensor in accordance with the temperature profile as the one or more eluted components are separated from the sample by the gas chromatograph; and
a candidate chemical identifier, communicatively coupled to the surface acoustic wave sensor, a set of one or more candidate chemicals for the eluted component of interest being identified by the candidate chemical identifier based on a corresponding peak of the surface acoustic wave frequency response data.

15. The system of claim 14, further comprising a temperature profile manager communicatively coupled to the candidate chemical identifier, the temperature profile being modified by the temperature profile manager based upon a result of the identification by the candidate chemical identifier.

16. A non-transitory program storage medium on which are stored instructions executable by a processor or programmable circuit to perform operations for identification of chemicals in a sample, the operations comprising:
receiving a temperature profile defining a varying target temperature as a function of time;
issuing a temperature control command to adjust a temperature of a surface acoustic wave sensor in accordance with the temperature profile as one or more eluted components are separated from a sample by a gas chromatograph, the surface acoustic wave sensor coupled with the gas chromatograph to define a gas chromatography/surface acoustic wave system in which the one or more eluted components separated from the sample by the gas chromatograph accumulate at a condensation spot on the surface acoustic wave sensor;
receiving surface acoustic wave frequency response data generated by the surface acoustic wave sensor, the surface acoustic wave frequency response data including one or more peaks corresponding respectively to the one or more eluted components separated from the sample by the gas chromatograph; and
identifying a set of one or more candidate chemicals for an eluted component of interest based on a corresponding peak of the surface acoustic wave frequency response data.

17. An apparatus comprising:
the non-transitory program storage medium of claim 16; and
a processor or programmable circuit for executing the instructions.

18. The apparatus of claim 17, further comprising:
a thermoelectric cooler configured to receive the temperature control command and adjust the temperature of the surface acoustic wave sensor based on the temperature control command.

19. The apparatus of claim 18, further comprising:
the surface acoustic wave sensor.

20. The apparatus of claim 19, further comprising:
the gas chromatograph.

* * * * *